United States Patent [19]
Dodson et al.

[11] Patent Number: 6,150,126
[45] Date of Patent: *Nov. 21, 2000

[54] DAPHNIA REPRODUCTIVE BIOASSAY FOR TESTING TOXICITY OF AQUEOUS SAMPLES AND PRESENCE OF AN ENDOCRINE DISRUPTER

[75] Inventors: Stanley I. Dodson, Cottage Grove; Christine M. Merritt, Madison, both of Wis.; Jonathan B. Shurin, Chicago, Ill.; Kristin Girvin Redman, Madison, Wis.

[73] Assignee: Wisconsin Alumni Research Foundation, Madison, Wis.

[ * ] Notice: This patent is subject to a terminal disclaimer.

[21] Appl. No.: 09/154,315

[22] Filed: Sep. 16, 1998

Related U.S. Application Data

[63] Continuation-in-part of application No. 08/762,382, Dec. 6, 1996, Pat. No. 5,932,436.

[51] Int. Cl.$^7$ .............................. C12Q 1/00; C12Q 1/02; G01N 33/53
[52] U.S. Cl. .............................. 435/29; 435/4; 435/967; 435/975
[58] Field of Search .............................. 435/4, 29, 967, 435/975

[56] References Cited

U.S. PATENT DOCUMENTS

| | | | |
|---|---|---|---|
| 4,965,202 | 10/1990 | Haley et al. | 435/170 |
| 5,169,777 | 12/1992 | Haley et al. | 435/252.1 |
| 5,416,005 | 5/1995 | Blankenmeyer | 435/29 |
| 5,481,815 | 1/1996 | Murphy et al. | 37/344 |
| 5,518,636 | 5/1996 | Petrille, III et al. | 210/749 |
| 5,665,555 | 9/1997 | Sweeney et al. | 435/7.21 |
| 5,672,470 | 9/1997 | Hengstenberg et al. | 435/4 |

OTHER PUBLICATIONS

American Society for Testing and Materials (ASTM), *ASTM Standards on Aquatic Toxicology and Hazard Evaluation*, Standard Guide for Conducting Life–Cycle Toxicity Tests with *Daphnia magna* (E1193–94), ASTM Publication Code No. 03–547093–16, ASTM, Philadelphia, PA, pp. 512–528 (1994).
U.S. Environmental Protection Agency, *Short–Term Methods for Estimating the Chronic Toxicity of Effluents and Receiving Waters to Freshwater Organisms*, EPA/600/4–91/002, Lewis et al. (ed.), Cincinnati, OH (Jul. 1994).
Soto et al., in Advances in *Modern Environmental Toxicology* 21:295–309, Chemically Induced Alterations in Sexual and Functional Development: The Wildlife/Human Connection, Colburn & Clement (eds.), Princeton Scientific Publishing Co., Inc., Princeton, NJ (1992).
Bhatnagar–M–C et al, in *Journal of Environmental Biology* 9(3 Suppl): 283–288; Abstract: Toxicity of a few Pesticides to a Freshwater Teleost. Clarias Batrachus (LINN) (1988).
Snell et al., *Environmental Toxicology and Chemistry* 14(3): 415–420 (1995).
Shurin et al., *American Society of Limnology & Oceanography*, Program and Abstracts, Jun. 16–20, 1996, Abstract: Toxicity and Environmental Sex Determination in Daphnia Pulex, University of Wisconsin–Milwaukee (1996).
Dodson and Hanazato, Abstract: Environmentally Induced Alterations in Development: A Focus on Wildlife, presented to Wingspread Conference Center, Racine, WI (Dec. 1993).
S. Kilham and C. Goulden, handout entitled COMBO Medium (1995).
Dodson et al, *Environmental Health Perspectives* 103(4):7–11, (1995).
Baldwin et al., *Environmental Toxicology and Chemistry* 14(6): pp. 945–952 (1992).
Colborn et al., *Environmental and Health Perspectives* 101(5): 378–384 (1993).
Lampert, *Int. Revue ges Hydrobiol* 66(3) 285–298 (1981).
U.S. EPA. Environmental monitoring and assessment program: Great Lakes monitoring and research strategy, Office of Research and Development, Environmental Research Laboratory–Duluth, Duluth, MN 55804; pp. i to vii; 2–7 to 2–9, 4–1 to 4–38, B–14, and B–18 to B–20 (1992).
Shurin, J. *Toxicity and Environmental Sex Determination in Daphnia*, submitted to the U.S. Environmental Protection Agency (EPA), Dec. 1995.
American Society for Testing and Materials (ASTM), ASTM Standard Guide for Conducting Renewal Life–Cycle Toxicity Tests with *Daphnia magna*, (E1193–94), Philadelphia, PA pp. 151–167 (1988).
Hanazato and Dodson, *J. Plankton Res.* 14(12): 1743–1755 (1992) (Abstract).
Hanazato and Dodson, *J. Plankton Res.* 15(9): 1087–1095 (1993) (Abstract).
Dodson et al., *Environmental Toxicology Chemistry* 14(1): 43–50 (1995) (Abstract).
Hanazato and Dodson, *Limnol. Oceanog.* 40(4): 700–709 (1995) (Abstract).
Zou and Fingerman, *Bull. Environ. Contam. Toxicol.* 58:596–602 (1997).
Hobaek and Larsson, *Ecology* 71(6): 2255–2268 (1990).

*Primary Examiner*—Christopher Tate
*Attorney, Agent, or Firm*—Whyte Hirschboeck Dudek S.C.

[57] ABSTRACT

The invention provides a Daphnia reproductive bioassay for detecting and confirming the presence of a toxic substance in an aqueous sample, and/or for screening the substance as an endocrine disrupter. According to the assay, a test sample is brought into contact with adult, oviporous Daphnia of a single clone under conditions of crowding and growth conditions to stimulate sexual reproduction and the production of males. The bioassay is based upon the measurement of endpoints that convey quantitative information about the biological activity of the substance: survivorship, numbers of female offspring, numbers of male offspring, number of resting eggs, number of offspring that display developmental deformities or behavioral abnormalities, and nutritional status of the offspring. Also provided are kits for use in conducting the bioassay.

20 Claims, 7 Drawing Sheets

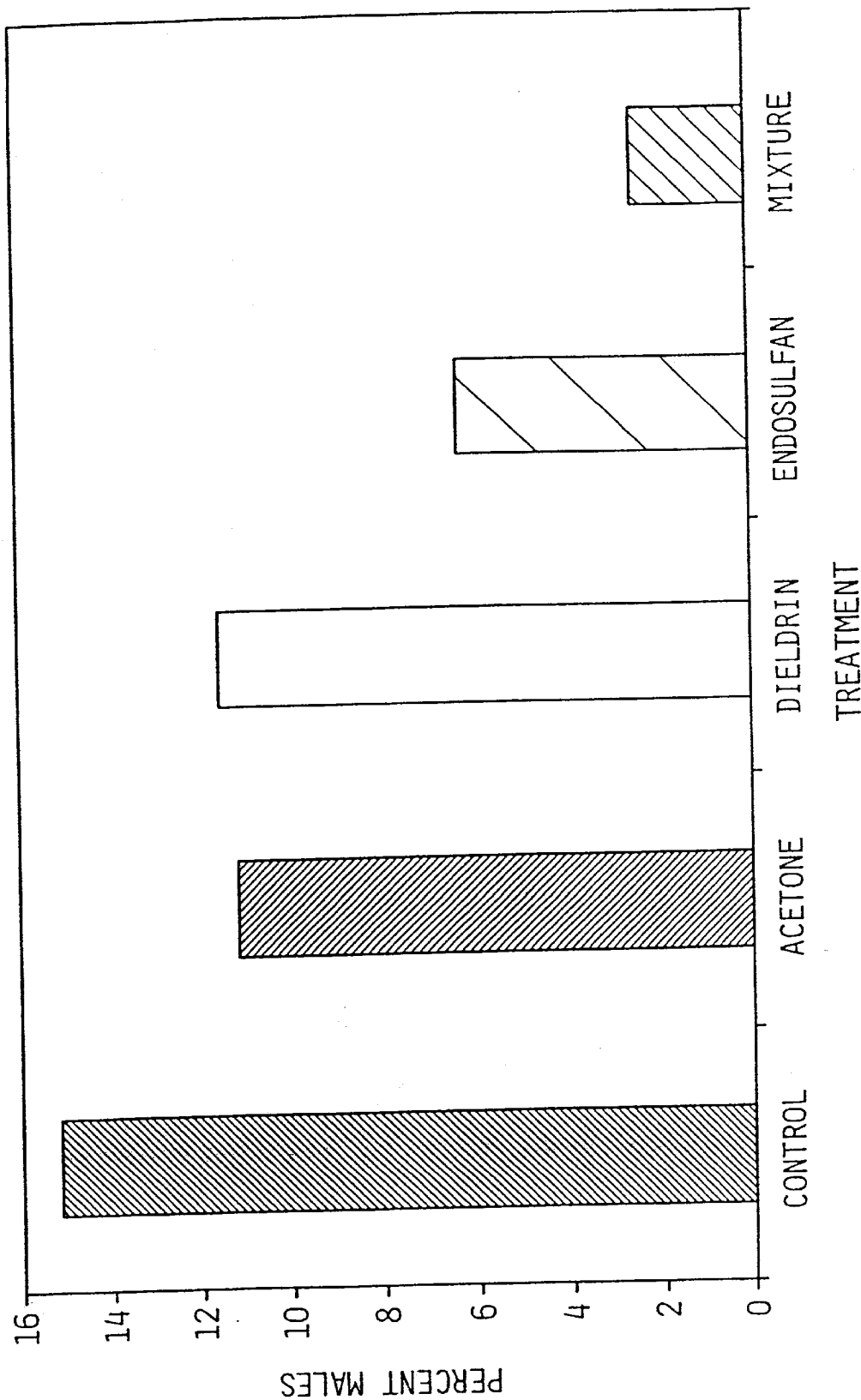

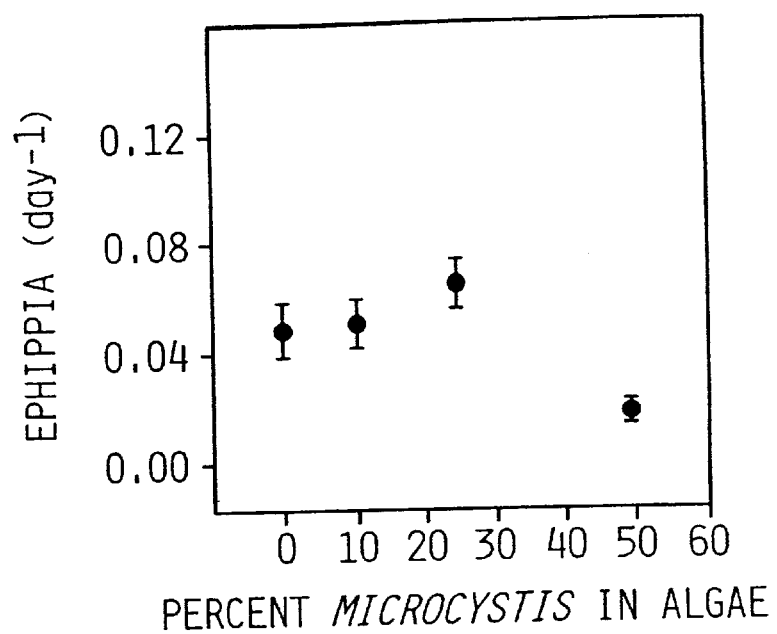
FIG_2a
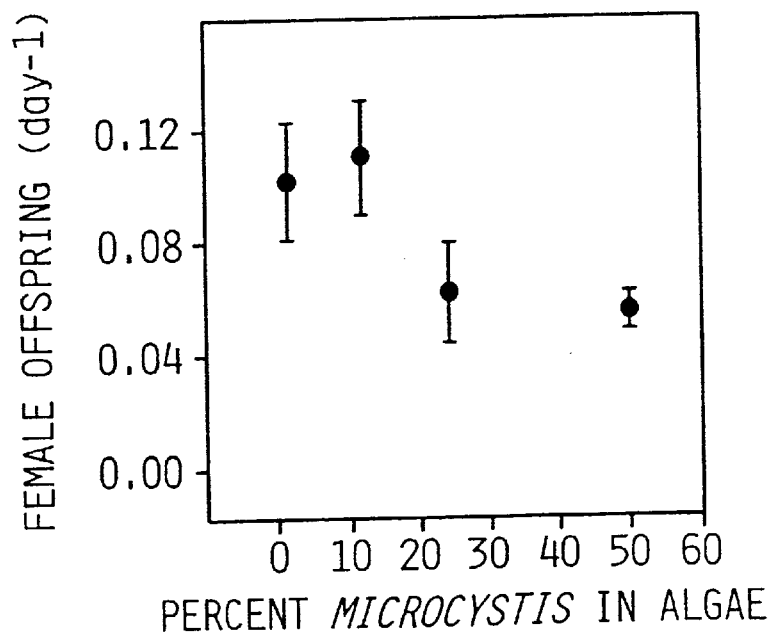
FIG_2b

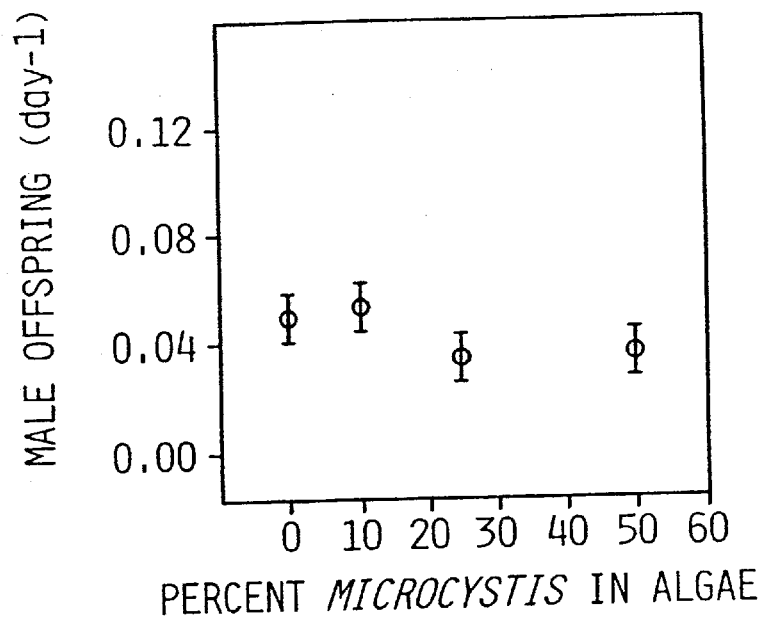
FIG_2c
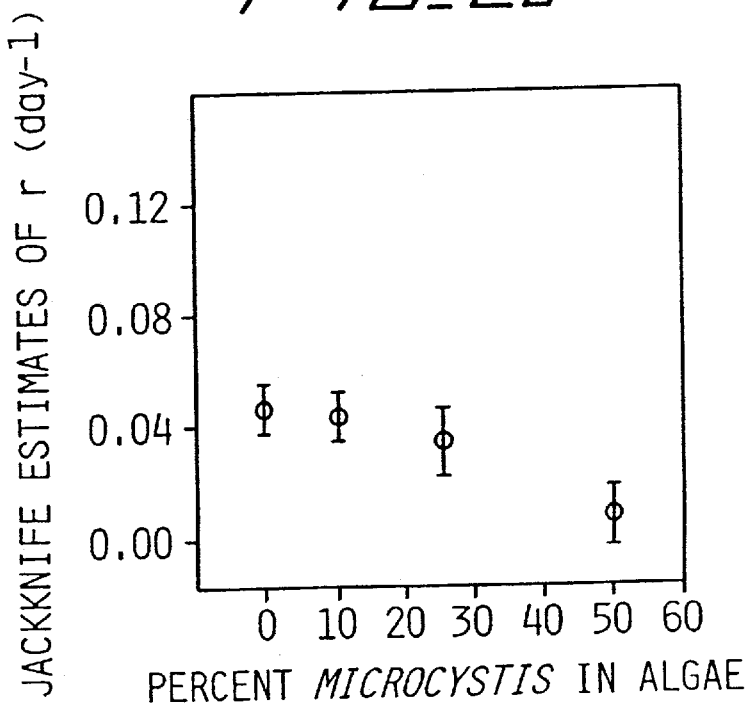
FIG_2d

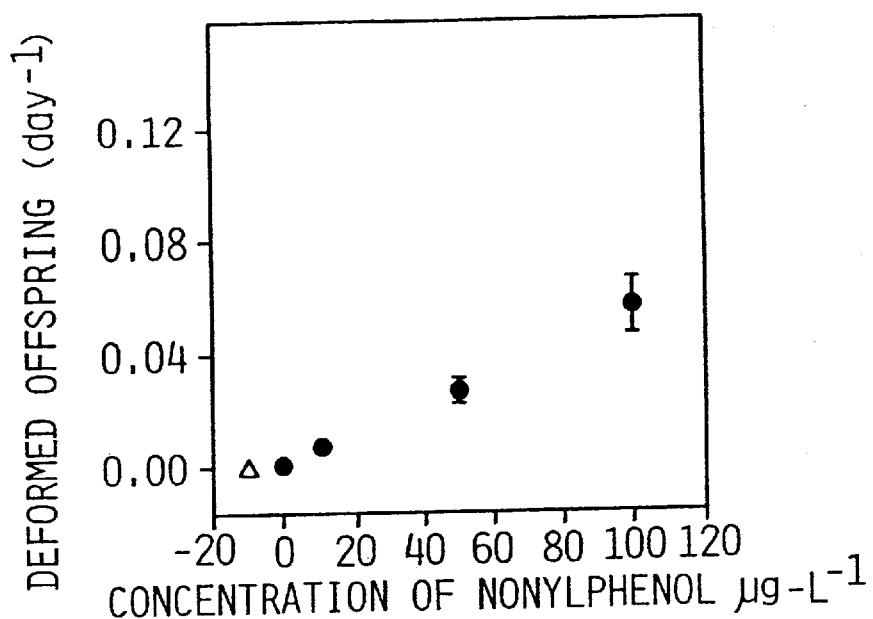
FIG_3a
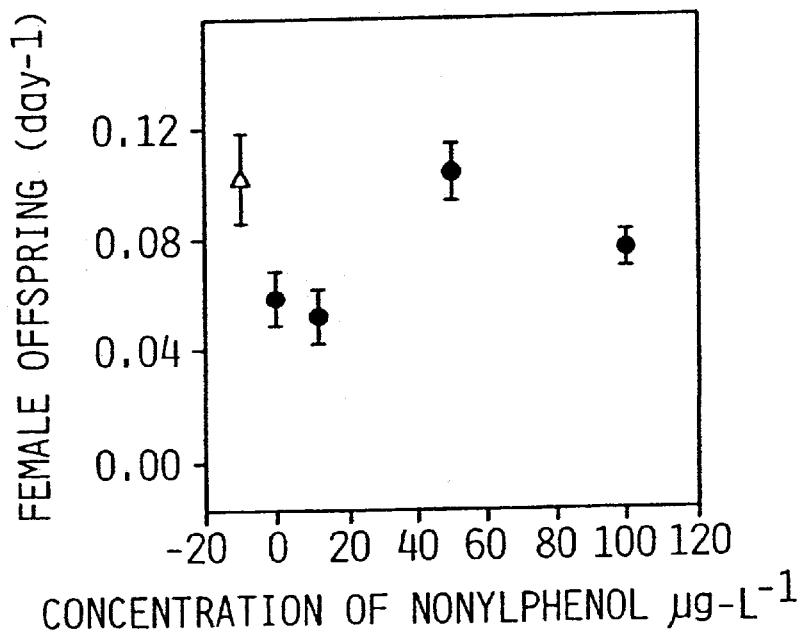
FIG_3b

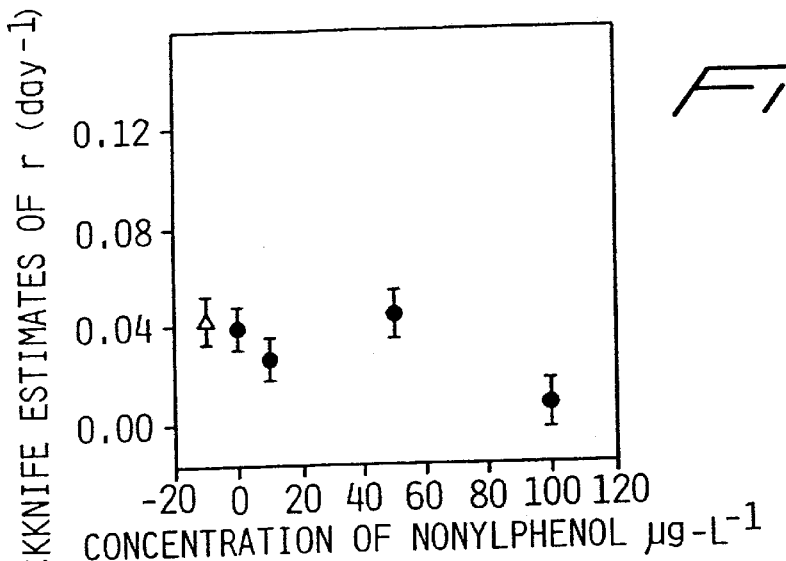
FIG_3c
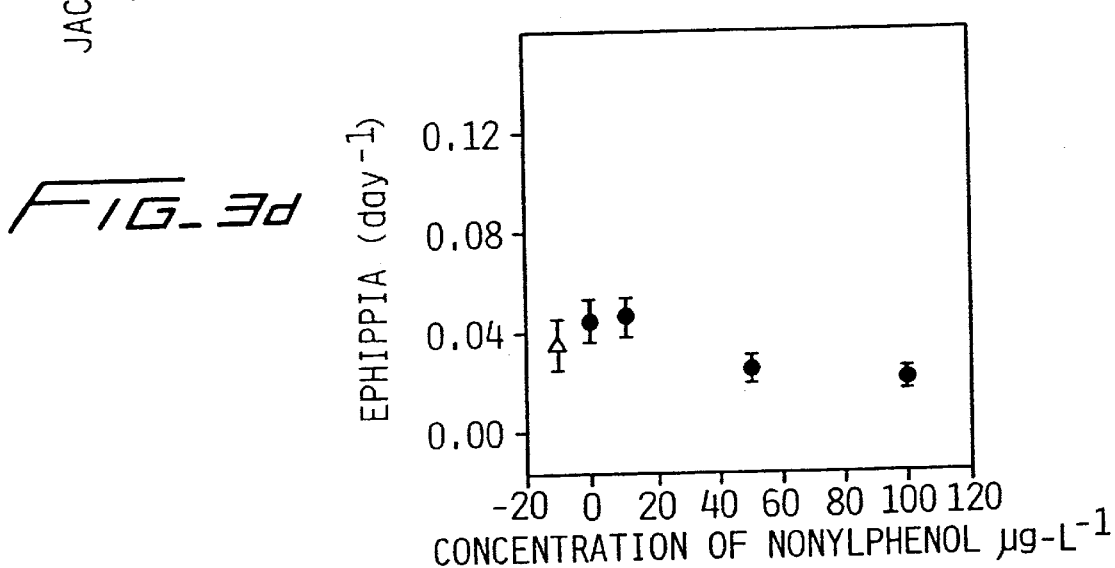
FIG_3d
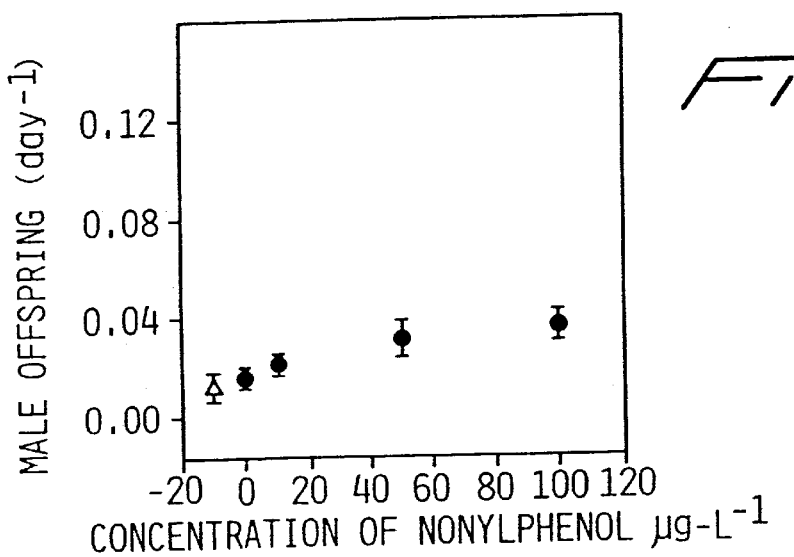
FIG_3e

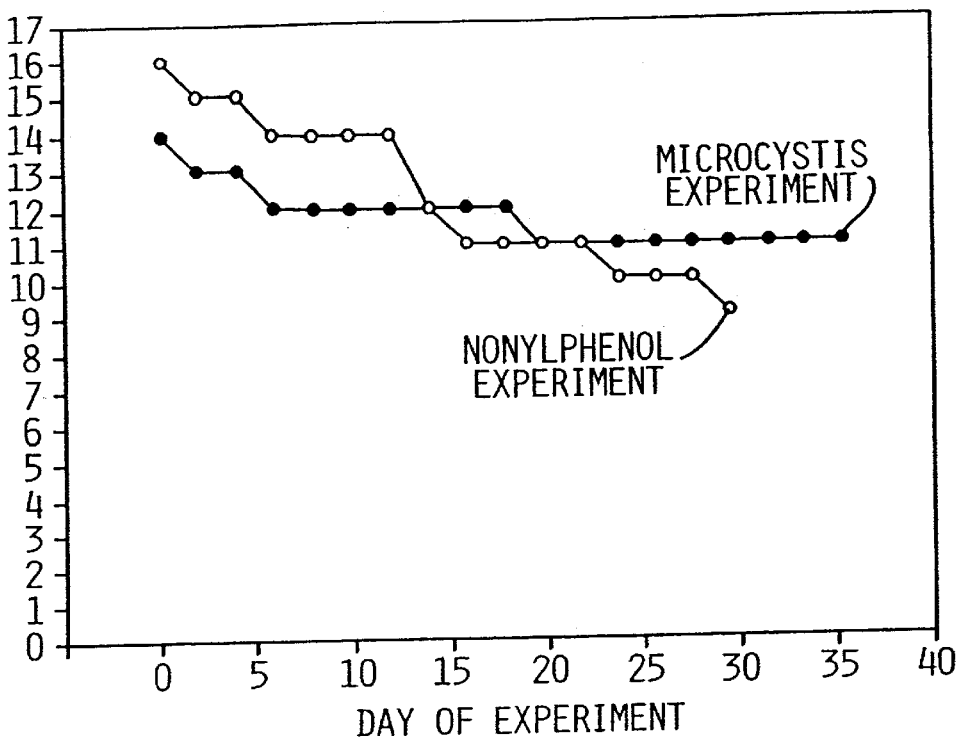
FIG_4a
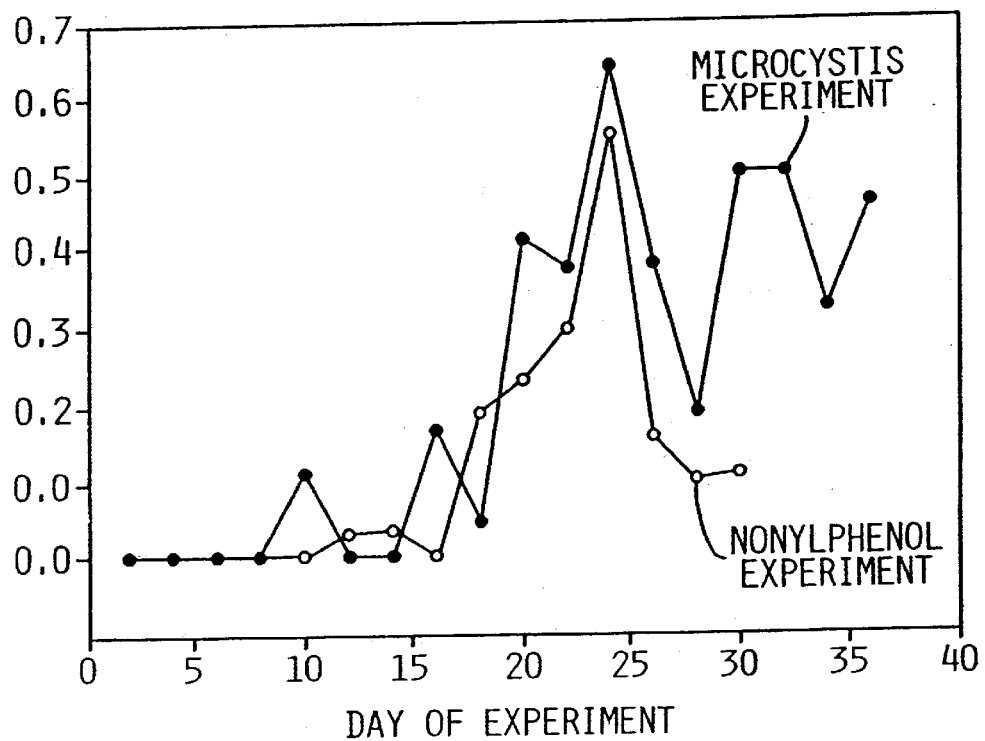
FIG_4b

DAPHNIA REPRODUCTIVE BIOASSAY FOR TESTING TOXICITY OF AQUEOUS SAMPLES AND PRESENCE OF AN ENDOCRINE DISRUPTER

CROSS-REFERENCE TO RELATED APPLICATIONS

This application is a continuation-in-part of U.S. patent application Ser. No. 08/762,382, filed Dec. 6, 1996, now U.S. Pat. No. 5,932,436.

GOVERNMENT SUPPORT

The invention described herein was made with assistance of a United States NSF Grant No. DEB-9632853. The Government has certain rights in the invention.

BACKGROUND OF INVENTION

In early toxicity tests of chemicals, the measured endpoint was acute toxicity. Over the past ten years, toxicity testing has expanded to include measures of subchronic toxicity including cancer, immune suppression, developmental effects and endocrine system disruption. Today, there is increasing concern about the long-term effects of anthropogenic chemicals such as polychlorinated biphenyls (PCBs), pesticides and plasticizers, among others, found in water, food, air and the materials around us. An increasing number of wildlife species are having reproductive difficulties, and there is current concern about declining sperm counts in human males.

Safe environmental concentrations of toxicants are those that allow humans and indigenous organisms in nature to complete their life cycles unimpaired. Toxicity tests that include exposure through the entire life cycle are the most useful tools for such measurements but can be too long and costly to be applied in most toxicity assessments. As a result, several short-term tests have been developed to estimate chronic toxicity, representing compromises of speed, sensitivity and cost. Most measurements of toxicity today rely on these short-term tests to indicate concentrations above which toxic effects are expected.

Daphnia are widely used in testing for aquatic toxins because of their rapid clonal reproduction, ecological importance, and sensitivity to their chemical environment. Toxicity tests using Daphnia have typically been used to detect changes in survivorship and fecundity.

Cladoceran zooplankton such as Daphnia can employ a reproductive strategy known as cyclical parthenogenesis in which one generation of sexual reproduction is interspersed with many generations of asexual reproduction. The ability to alternate life history strategy allows cladocerans such as Daphnia to achieve a high reproductive rate asexually when conditions are favorable, and to produce offspring sexually for survival when the environment becomes unsuitable. Under favorable environmental conditions, Daphnia reproduce asexually by producing eggs that hatch into female offspring that, in turn, asexually produce eggs that also hatch into female offspring, and so on. Populations can achieve high growth rates during the asexual phase as females mature in 8 to 11 days. The Daphnia population in Lake Mendota, Madison, Wis., is typically entirely female with occasional males and sexual females in late summer.

Sexual reproduction is initiated when females produce males and haploid resting eggs under certain conditions such as crowding, food scarcity, low temperatures, short photoperiod, or chemical cues emitted by predators. Males mate with sexual females to produce resting eggs that can persist in a dormant state for years, allowing the population to survive hard times. Fertilized zygotes develop into embryos that enter diapause. These embryos are contained in a durable ephippium and can remain viable for years in sediments before hatching in response to environmental cues. Production of ephippia can be essential to maintain a Daphnia population in an environment that periodically becomes inhospitable.

Bioassays that employ Daphnia are used to monitor and give a rough indication of the level of contamination in waters, and to test a specific chemical to predict the risk posed to biological communities. There are several standard assays that presently use Daphnia for measuring the toxicity of chemical substances in an aquatic sample. One such bioassay has been developed by the U.S. Environmental Protection Agency (EPA) to assess the relative toxicity of effluents and surface waters (U.S. EPA, "Short-term methods for estimating the chronic toxicity of effluents and receiving waters to freshwater organisms"(3d ed.), Section 13, Daphnid, *Ceriodaphnia dubia*, Survival and Reproduction Test, Method 1002.0, Lewis et al. (eds.), Environmental Monitoring Systems Laboratory, Cincinnati, Ohio (EPA/60014-91/002, July 1994)). The EPA bioassay employs neonates (<24 hours old) of *Ceriodaphnia dubia* during a three-brood, 7-day static renewal test, with test results measured in terms of survival and reproduction.

Another bioassay that is currently used is a 21-day test provided by the American Society for Testing and Materials (ASTM) to examine the toxicity of a water sample or other material (ASTM Standards on Aquatic Toxicology and Hazard Evaluation, Standard Guide for Conducting Renewal Life-Cycle Toxicity Tests with *Daphnia magna*, Method E 1193-87, Philadelphia, PA (ASTM PCN 03-547093-16, May 1988). The ASTM Daphnia assay is labor-intensive and the organisms are grown at high food levels which involves regularly changing water to keep the organisms well fed and maximally reproducing. A single organism is placed into each of ten separate vials, the test is run for 21 days, and the endpoint measurement is the total number of surviving organisms. Under these conditions, the Daphnia produce female offspring by asexual reproduction.

A drawback of the EPA and ASTM Daphnia bioassays is that the assays only consider the effects on Daphnia during the asexual phase of their life cycle. In those bioassays, the animals are grown under conditions that optimize growth and asexual reproduction. However, projections of the species, community or ecosystem level risk posed by waterborne contaminants based on bioassays of asexual reproduction may ignore serious effects on reproductive strategy. Such bioassays can miss or make false predictions about the real effects of toxic chemicals in the environment because they do not measure toxic effects during a fundamental part of the life cycle of the model organism. All animals show variable sensitivity at different points in their development and over the course of an annual cycle. Invertebrates such as Daphnia with complex, multi-stage life histories may be especially useful sentinels for these complex sensitivities. Moreover, effects of toxins on various life stages can have entirely different consequences if exposure coincides with sub-optimal environmental factors. An assay is needed that can measure these effects at every stage of development in conditions that reflect those in nature.

Other disadvantages of the EPA and ASTM assays are that they tend to provide inconsistent and highly variable, irreproducible results within and between laboratories, do not measure the effects of contaminants on production of males, and provide no information on sex ratio or on developmental changes.

Daphnia bioassays have been disclosed that subject the organism to stress to measure survivorship. See for example, U.S. Pat. Nos. 5,481,815 (Murphy) and 5,169,777 (Haley) which describe a 48-hour toxicity bioassay using *Daphnia magna* neonates. Drawbacks of such assays are that they measure only strong (e.g., acute) effects of a contaminant and fail to detect subtler effects that may be ecologically important, and give no information on male production or sex ratio or resting egg production. Anthropogenic chemicals interact with developmental pathways of many different animals, and invertebrates such as Daphnia which have alternate life history patterns may be susceptible to different chemical interactions during its two stages of reproduction. Such effects would not be detected in a 48-hour bioassay. Furthermore, a 48-hour bioassay would not detect the consequences of toxic effects on sexual reproduction of Daphnia which can appear in depressed hatching of resting eggs.

Many pesticides, toxic xenobiotics such as some PCBs and dioxins, and common industrial chemicals such as nonylphenol and phthalates, affect and disrupt the endocrine system of an animal (i.e., endocrine disrupter). Such chemical substances can function as estrogen mimics and are implicated as agents that interfere with male development in wildlife populations such as alligators, sea gulls, turtles, salmon and trout. Endocrine disrupters affect the life history of Daphnia by triggering or suppressing the production of males and resting eggs, and/or cause visible developmental deformities in the offspring. For example, low levels of the plasticizer nonylphenol have been shown to reduce resting egg production, and cause a characteristic deformity by preventing normal development from the embryo to the neonate stage. However, there is no bioassay currently available to quickly and reliably test for the presence of endocrine disrupters in a water sample.

Accordingly, an object of the invention is to provide a bioassay that is relatively easy to perform, fast, highly accurate and sensitive, and provides ecologically meaningful test information to evaluate environmental toxicity. Another object is to provide a test assay that is highly consistent within and between laboratories. Another object is to provide a bioassay and test kit for detecting toxic substances in a sample and to relate such toxicity to a particular type of chemical agent. Yet another object is to provide a bioassay that can be used to detect the presence of an endocrine disrupter, including estrogen mimics in a water sample, and to test the activity of a chemical substance for activity as an endocrine disrupter.

SUMMARY OF THE INVENTION

These and other objects are achieved by the present invention which is directed to a Daphnia reproductive bioassay and kits for use in conducting the bioassays. The present Daphnia bioassay can be used to quickly assay an aquatic sample for the presence of a toxic substance and the relative level of toxicity of the sample. The bioassay can also be used for assaying an aqueous sample for the presence of a chemical substance having activity as an endocrine disrupter, e.g., a substance that can affect the endocrine system of an animal, and reproduction strategies and/or neonate development.

Additionally, the assay can be used for screening and testing a chemical substance for toxicity, and its biological activity as an endocrine disrupter. The assay is also useful for determining concentrations of a chemical substance, or of a test sample containing a chemical substance, that has a toxic effect and/or an observed endocrine disrupting effect on the biological functions of an animal. The assay of the current invention can quickly establish the concentration or level of toxin whereby no toxic response is seen, on the lowest concentration or level at which a response is seen.

The Daphnia reproductive bioassay features measuring various endpoints that convey quantitative information about the toxicity and/or the effect of biologically-active chemicals in an aqueous sample on the life history of Daphnia. The endpoints that are measured can include: survivorship and mortality of adult females, survivorship and mortality of male and female neonates (newly-born offspring), total number of offspring or neonates, sex ratio, number of resting eggs, observed developmental deformities in offspring, observed behavioral abnormalities in offspring, and nutritional status of offspring. At the end of the test period, or optionally at intervals during the assay, the endpoints are measured and comparisons are drawn between the test sample and the control.

The assay involves growing adult, oviparous Daphnia of a single clone under environmental growth conditions that will induce sexual reproduction by which the Daphnia will produce both male and female offspring. The assay is conducted by preparing an aqueous control and test sample that are each combined with a Daphnia food source. The test sample contains an aliquot of a sample to be tested in an aqueous medium, for example, a water sample, industrial effluent, elutriate of soil, and the like, or a particular chemical substance (known or unknown) to be tested.

An effective number of Daphnia adult females are placed in a volume of the aqueous control and test sample for crowding, for example, in about 30-ml volume of liquid containing at least three (3) Daphnia. The same number of Daphnia are added to each of the controls and the test samples. The Daphnia are subjected to a photoperiod of short day length of about 6–9 hours light:18-15 hours dark at a temperature of about 17–25° C., preferably about 20–22° C. The assay can be conducted at a normal or increased food level in order to maximize developmental rate and fecundity. The bioassay employs a clone of Daphnia that grows well in the laboratory and reliably produces males in control cultures.

The environmental ("control") conditions are optimal for producing males while maintaining fecundity and survivorship, but sub-optimal for producing maximum fecundity in order to somewhat stress the Daphnia (as they are often in nature). Under such conditions, the Daphnia are more likely to respond to very low but ecologically important and/or environmentally relevant levels of toxic chemicals in the test treatments. The controls are examined to confirm, on average, a zero to low mortality of the adult females, a sex ratio with a proportion of males at about 5–70% of the total offspring, and a lack of resting eggs.

The assay is conducted to optimize the exposure of offspring (neonates) to the test sample and the control medium, and to assure that the neonate Daphnia that are included in the calculation of the endpoints of the bioassay have been exposed only to the substance(s) in the test sample and control medium, and do not reflect the effect of another substance. To that end, it is preferred that the assay period is at least about 4–7 days in length. After about 34 days from the start of the bioassay, the neonate Daphnia within the test sample and control medium are discarded, and the adult Daphnia from each are placed in fresh control or test sample medium. The length of the assay can be increased to include testing multiple generations of Daphnia.

In screening for toxicity, the test sample or chemical substance can be prepared as a series of aqueous dilutions, and tested according to the bioassay to determine the lowest (sublethal) concentration that has a toxic effect on Daphnia. Survivorship and fecundity are measured to confirm that the test sample contains sub-lethal levels of the sample or chemical substance being tested. A high level of survivorship of adults and neonates indicate a sublethal level of a chemical substance.

In assaying for activity as an endocrine disrupter, a sublethal concentration of a chemical substance or test sample is tested. Measuring the sex ratio, morphological abnormalities and/or resting egg production provides an indication as to whether the sample or chemical substance has activity as an endocrine disrupter and affects female reproduction and/or neonate development. The presence of an endocrine disrupter substance in the test sample is indicated by the endpoint measurements showing a significant variance or statistical difference relative to the control, i.e., at the $\alpha=0.05$ level. For example, an endocrine disrupter substance in the test sample can be indicated by a statistically higher or lower sex ratio than the control, a difference in the number of resting eggs, and/or the presence of or a higher number of offspring (neonates) with a morphological (developmental) deformity. After screening the unknown chemical substance or test sample for endocrine disrupter activity, the substance or the test sample can be subsequently analyzed to methods known in the art, to further characterize or determine the specific identity of the endocrine disrupter substance.

The invention further provides a kit for conducting the bioassay. The kit can include containers, a device for manipulating the Daphnia test organisms, cultures of a Daphnia clone, algal food species, and instructional materials for culturing the Daphnia and algae, for conducting the assay and scoring the results, and other like materials for conducting a bioassay.

The present bioassay is superior to other methods of biotesting for toxic effects of chemicals dissolved in water, at least in part because its measurements can include the effects of potential toxicants on developmental integrity, sex ratio and resting egg production as well as survivorship and fecundity of offspring or neonates. These additional endpoints are more informative and sensitive endpoints than survival and fecundity. The present Daphnia reproductive bioassay provides an indication of hormone-like chemical toxins in water that are ecologically important and/or environmentally relevant but may not reduce either short-term fecundity or survivorship. In addition, the Daphnia reproductive bioassay can provide an insight into the mechanism of toxicity, where other assays only indicate the presence or absence of toxicity. The information generated from the present bioassay can also reduce the need for expensive chemical analysis, thereby reducing overall costs in monitoring for chemical substances.

The Daphnia reproductive bioassay of the present invention is useful in biomonitoring laboratories of the federal and state government, and private laboratories such as those of large chemical companies. The assay can be used to (1) evaluate the toxic effects of individual chemical formulations for product testing as required by the Food and Drug Administration (FDA), (2) for pesticide registration as required by the U.S. Department of Agriculture (USDA), and (3) to screen natural waters or effluents from industry or municipalities for toxic potential for mandated testing required by programs of the Environmental Protection Agency (EPA) such as the National Pollutant Discharge Effluent, Superfund, and the Resource Conservation and Reclamation Act programs.

BRIEF DESCRIPTION OF THE DRAWINGS

FIG. 1 is a graphical comparison of the effects of 100 $\mu$g per liter of two pesticides, dieldrin and endosulfan.

FIGS. 2($a$)–($d$) are graphical illustrations of the results of the Microcystis experiment. All data are numbers of offspring per female per day. Bars (1) are standard errors.

FIGS. 3($a$)–($e$) are graphical illustrations of the results of the nonylphenol experiment. Notation is the same as in FIG. 2. The open triangle (A) is the acetone control.

FIGS. 4($a$)–($b$) are graphical comparisons of the medium controls in the Microcystis and nonylphenol experiments.

DETAILED DESCRIPTION OF THE INVENTION

Figure 5:
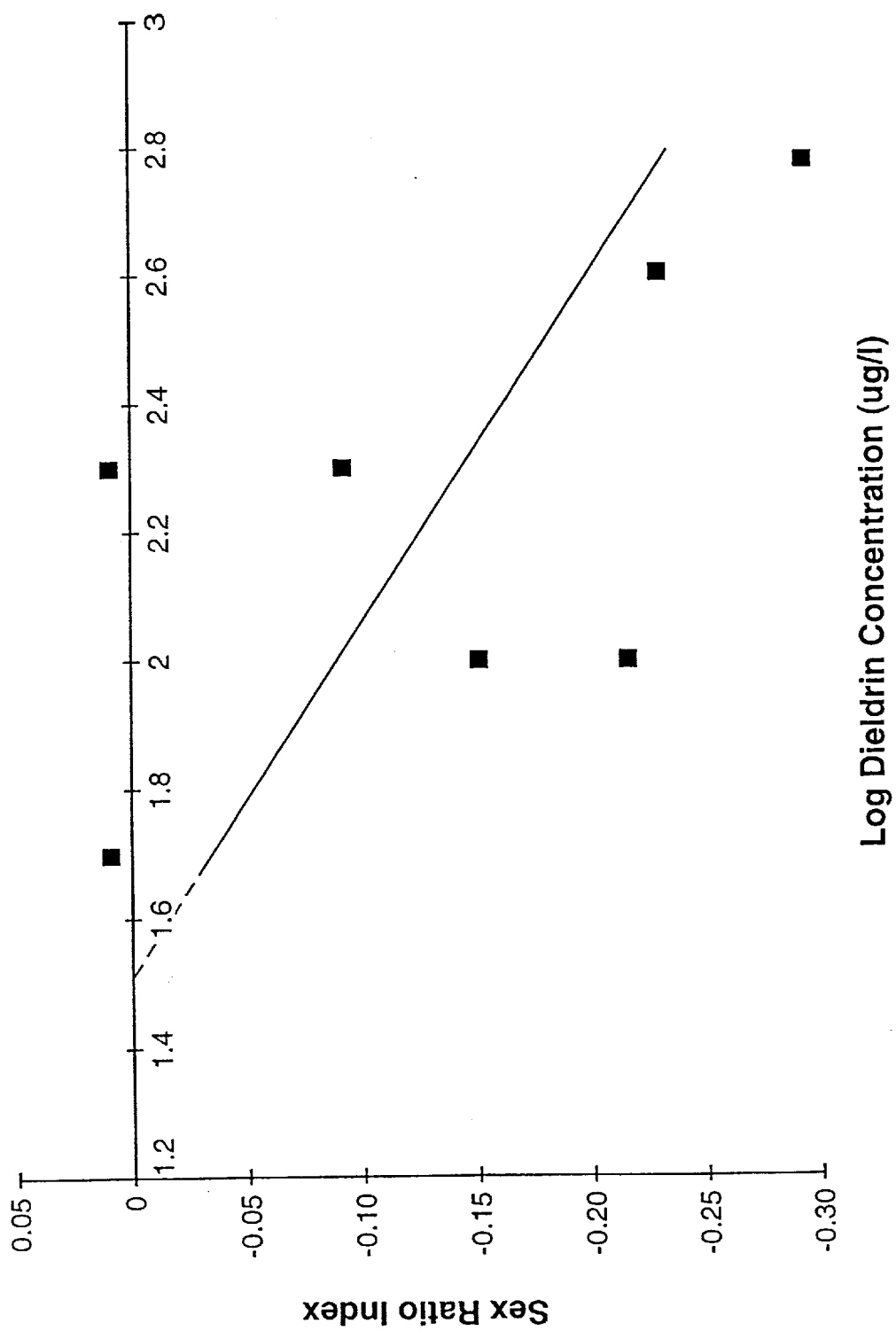
FIG. 5 is an illustration of the sex ratio index as the difference between a dieldrin treatment and its control (after using arsine transformation of the data). The line is the best-fit linear regression line of sex ratio index and the $\log_{10}$ of dieldrin concentration. The dashed line ( - - - ) shows time extrapolation to the concentration of no effect (at about 30 ppb dieldrin).

The present Daphnia reproductive bioassay uses production, survival and gender of the Daphnia clone under controlled conditions, and involves measuring endpoints that convey quantitative information about a biologically-active agent in the sample. The assay can be used for examining not only toxicity of chemical substances in a test sample but also the mechanism that underlies the physiological stresses on reproduction, development and growth resulting from the toxic effect. The assay can be used to detect and confirm the presence of sublethal toxic levels of a chemical substance in an aqueous sample, and to indicate the nature of the chemical substance as one that is an endocrine disrupter, i.e., can affect the endocrine system of an animal. The assay can also be used to screen a substance for activity as an endocrine disrupter.

The assay is run with controls, and treatments or test samples. The test sample uses the same medium and conditions as the control with the addition of a sample to be tested. Samples that can be tested according to the present Daphnia reproductive bioassay can be taken, for example, from a natural water source such as a river, natural lake, municipal water supply lake, domestic drinking (tap) water, storm water, ground water, an industrial effluent, municipal effluent, or sewage influent or effluent, or a synthetic testing medium as in the case of product testing. The test sample can also be an extract or elutriate from solid samples such as, for example, soil, aquatic sediment, sludge, wood, plant material, paper or pulp. The solid sample can be extracted with the growth medium for about 12 hours or other suitable time period, centrifuged, and the elutriate then tested.

A useful experimental unit is a small jar or other receptacle for containing the growth medium for the Daphnia and an effective number of adult egg-carrying female clone mates of a Daphnia clone to facilitate crowding and the production of male offspring. To induce sexual reproduction, the experimental units (control and test samples) are subjected to a short daylight photoperiod of about 6–9 hours light and about 15–18 hours darkness, and a temperature ranging between about 17–25° C. The control(s) and test samples can be placed in an environmentally-controlled chamber with photoperiod and temperature controls. In a preferred set-up, the control and test sample are replicated to provide multiple experimental units (containers) for each control or test sample, for example 12–15 units.

In an example of a useful set-up of the bioassay, the control conditions are as follows: about 30-ml of a growth medium and algae food source for the Daphnia (with no added chemical or test sample), a temperature of about 17–25° C., preferably about 20–22° C., and a light:dark photoperiod of about 6–9:18-15 hours, preferably about 6:18 hours. In a 30-ml volume, at least three (3) adult female Daphnia are included to provide crowding, preferably 3–10 adults, more preferably 5–9 adults.

The developmental time of Daphnia eggs in the brood chamber of the adult female is about 3–4 days whereupon the adult Daphnia molts and releases the neonate. To ensure that the neonates that are examined and included in the data collection at the end of the assay underwent their entire development within the control or test sample solutions, neonates produced during at least the first 3–4 days of the assay are removed and discarded. Thus, the assay is commenced and, after an interim time period, the growth medium is renewed, the adult Daphnia are removed by pipette, sieve or other means, and transferred into new containers of fresh growth medium and algae, and the neonates are discarded.

After an additional time period of 1–7 days, preferably about 3–4 days, the adults and neonates produced during that interim period are scored according to the bioassay endpoints. Thus, the bioassay can be conducted over a minimum period of about 1–7 days with a medium renewal after the initial 3–4 days of the assay. The length of the assay can be increased to include testing of multiple generations of Daphnia, with a change of growth medium as needed to maintain an adequate food level to sustain growth during the assay. The bioassay can include the additional step(s) of confirming the activity of the chemical substance in the test sample as an endocrine disrupting substance, and/or determining the identity of the chemical substance by conducting a further chemical or biological assay as known and used in the art.

In testing a water sample or chemical substance for bioactivity, it is advantageous to initially determine the sublethal concentration of the chemical substance or sample, particularly in cases of suspected high levels of toxicity. The sublethal concentration of a substance or sample is the highest concentration at which the substance or sample has no effect on survivorship or fecundity. Survivorship is measured by (expressed by) the number of adults surviving in the test sample compared to the control treatments. Fecundity is measured by the total number of offspring produced per adult female at the end of the assay in the test sample, compared to total offspring per adult female in the control treatments.

The sublethal concentration can be determined by preparing the test sample as a series of dilutions to provide a range of concentrations, for example, 10, 50, 100, 200, 400 µg per liter, or 100%, 80%, 60%, 50%, 30%, 10% effluent or test sample, and conducting the assay with the appropriate control(s). The sublethal concentration is determined by comparing fecundity and survivorship in the dilutions and the control to determine the dilution having the highest concentration of the test substance at which survivorship and fecundity are maintained at about the same level as the control. That dilution of the test substance can then be used as the test sample in the bioassay.

The growth medium employed in the bioassay is used to culture both the algal food source for the Daphnia and the Daphnia clone itself. The growth medium includes an effective level of nutrient salts to grow the algae but not interfere with the normal growth and development of the Daphnia. A preferred growth medium is an artificial lake water medium developed by S. Kilham and C. Goulden (personal communication), as described in Example 1.

The growth medium is combined with an initial level of algae as a food source that is sufficient to maintain Daphnia survival and reproduction during the prescribed time interval (s) of the test period, for example, the initial 3–4 day interval of a 6–7 day assay, whereupon the growth medium/algae food source is changed and renewed for an additional 3–4 day period. A preferred food source is an about 1:1 mixture of two green algae, *Chlamydomonas reinhardti* and *Selenastrum capricornutum*. These algae are commercially available from the Culture Collection & Algae, Department of Botany, University of Texas at Austin, Austin, Texas 78713-7640. The algal mixture is provided at an initial level to maintain growth of the Daphnia over the interim(s) of the test period. Preferably, the growth medium contains the algae at a level of about $5 \times 10^5$ cells per ml, which is about 6.9 mg carbon per ml. The algae are allowed to settle out between changes of the growth medium. Other algae that may be used as the food source include *Selenastrum minitum, Ankistrodesmus convolustrus,* and *A. falcatus,* and the like, optionally with a diatom such as *Nitschia frustulum* as a dietary supplement.

The bioassay uses a clone of the freshwater cladoceran Daphnia grown under defined, standardized conditions that cause the Daphnia to sexually reproduce to produce both male and female offspring. By comparison, in currently known Daphnia bioassays of toxicity only female offspring are produced under the environmental conditions that are used. The present Daphnia reproductive assay requires male production in the control so that the comparison of the sex ratio of the control with that of the test sample(s) illuminates the biological activity of the chemical substance.

Suitable Daphnia clones for the Daphnia reproductive assay are characterized by: (1) low mortality in the control treatment (the standard EPA criterion is less than 20% mortality); (2) consistent performance (reproduction and development) in control conditions; (3) ease of handling; (4) avoidance of the growth medium surface film in the experimental jars; (5) reliable reproduction; (6) production of males; and (7) production of resting eggs under control conditions.

Daphnia clones can vary in their reproductive strategy and not all Daphnia clones produce males or resting eggs. Daphnia clones suitable for use in the assay can be screened by running repetitive tests of the bioassay under control conditions. Such conditions include the same growth medium, algal food source, temperature, test period, photoperiod, pH, and medium renewal. A preferred Daphnia clone is one that will consistently and repeatedly produce about 5–70% males of the total number of offspring neonates in repetitive tests under controlled conditions, preferably about 20–70% males, more preferably about 40–60% males.

A useful clone in the present assay is *Daphnia pulicaria* [Georgia] which has demonstrated a consistent production of about 5–50% males under control conditions, and is available from BioAssay, Inc., Madison, Wis. Another Daphnia clone that consistently produced about 15–50% males under the above control conditions is *Daphnia galeata mendotae* Wingra CDF-1 clone. Other Daphnia clones that were screened and found to produce a lower percent of males include, for example, *Daphnia galeata mendotae* Oneida clone, and *Daphnia pulex* clones K, SBL and 9A-25 (Innes). Daphnia clones that were found to produce ephippia, such as *Daphnia hyalina* Stich clone, *Daphnia lumholtzi* Texas clone and *Daphnia pulex* clone A, are also useful in the bioassay.

The adult and neonate Daphnia are scored at the end of the bioassay according to a set of endpoints that convey quantitative information about the toxicity and/or the biological effect of a chemical substance on the life history of Daphnia, i.e., production, survival and gender of the Daphnia clone under test conditions. The endpoints that are measured can include:

1) survivorship of adult females;
2) survivorship of male and female neonates (newly-born offspring);
3) total numbers of offspring;
4) male:female sex ratio;
5) sex ratio, i.e., total number males:total number offspring (neonates);
6) number of resting eggs;
7) nutritional status;
8) developmental abnormalities; and
9) behavioral abnormalities.

To score the Daphnia at the end of the bioassay, the growth medium and the adult/neonate Daphnia can be poured into a container such as a petri dish. The water is removed, for example, using a large-bore pipette whose opening is covered with 120 μm nylon mesh. A smaller pipette, similarly covered with mesh, can be conveniently used to remove remaining water so that the Daphnia are caught in the surface film of a thin layer of water remaining in the container (e.g., petri dish). Care should be taken to avoid trapping Daphnia on the mesh, for example, by placing a drop of water back into the container. The container can be moved to a dissecting microscope and the entire surface scanned for living and dead Daphnia. This procedure can be repeated for each jar or container, e.g., experimental unit. Results can be recorded on a score sheet, including data on the date, time, number of resting eggs, and number, condition, stage and gender of the observed Daphnia.

In scoring the Daphnia, males and females can be distinguished by the shape of the rostrum (long and pointed in females, short and rounded in males), and the length of the first antennae (shorter than the rostrum in females, longer than the rostrum in males (elongated and cigar-like). Ephippia or "resting eggs" are distinguished from normal ("subitaneous") eggs by pigmentation (resting eggs are opaque and black or brown; normal eggs are mostly clear normal eggs). In addition, resting eggs are held in a thickened and black brood chamber, while normal eggs lie in a transparent brood chamber. Offspring are distinguished from adult females and mates by being less than half as long as the adults.

Offspring are scored for gender, and examined for gross and visible morphological deformities and abnormalities, and any behavioral abnormalities. Morphological abnormalities include, for example, reduced or absent terminal setae on the second antennae (swimming appendages), short or blunt or forward-curved tail spine, rounded helmet, a missing eye, neck teeth, or increased spine or helmet length. Behavioral abnormalities include, for example, abnormal swimming behavior, and abnormal motility. Such morphological and behavioral abnormalities indicate a teratogenic effect and interference of early development by a chemical substance.

Nutritional status can be measured by counting the number of lipid droplets along the backbone of the neonates and provides an indication of energy stores collected by the mother and deposited in the eggs. For example, a high number of lipid droplets (about 3–20) indicates optimal nutrition whereas a lower number of lipid droplets (about 0–2) indicates poor nutrition. A low number of lipid droplets indicates the presence of a chemical substance that interferes with lipid metabolism.

The presence of a toxic substance in a test sample is indicated by a statistically significant ($\alpha=0.05$) difference in one or more of the following parameters, based on a statistical analysis:

1. significantly lower survivorship of adults in the treatment (test be at least about 80% over six days);
2. significantly fewer neonates produced in the treatment compared to the control fecundity;
3. significantly fewer neonates surviving in the treatment (indicated by the number of dead neonates observed at the end of the six day test period) compared to the survivorship of neonates in the control; and/or
4. significantly higher or lower number of lipid droplets along the backbone of the neonates in the treatment compared to the control.

The presence of an endocrine disrupter substance is indicated by a statistically significant ($\alpha=0.05$) difference in one or more of the following parameters (which may or may not occur without any of the above-listed parameters that indicate overt toxicity):

1. significant increase or decrease in the sex ratio in the treatment compared to the control;
2. significant increase in the number of resting eggs in the treatment compared to the near zero number of resting eggs in the control;
3. significant increase in number of morphological abnormalities in the treatment compared to the near zero abnormalities in the control;
4. significant increase in behavioral abnormalities in the treatment compared to the near zero abnormalities in the control; and/or
5. significant increase or decrease in the number of lipid droplets along the backbone of neonates in the treatment compared to the control.

The assay is useful for detecting the presence of a chemical substance that has a biological effect on the endocrine system of an animal. An endocrine disrupter is an exogenous agent that interferes with the synthesis, secretion, transport, binding action, or elimination of natural hormones in the body that are responsible for the maintenance or homeostasis, reproduction, development and/or behavior, as described by Crisp et al., Risk Assessment Forum, US EPA, EPA/630/R-96/012 (Feb. 1997). Examples of chemical substances that are toxic and known or suspected endocrine disrupters that can be detected using the present bioassay include: herbicides such as dicamba, atrazine and other triazines; insecticides such as dieldrin, endosulfan, chlorpyrifos, pentachlorophenol (PCP), and dichlorodiphenyl-trichloroethane (DDT); phytohormones such as coumestrol; mycotoxins such as zearalenone and zearalenol; artificial hormones such as diethylstilbestrol (DES); industrial chemicals such as plasticizers, surfactants and residues thereof, nonylphenol and related alkylphenols, and phthalates; drugs such as tetrahydrocannabinol; food additives such as colorings and preservatives; natural toxins produced by cyanobacteria such as *Microcystis aerugenosa;* certain organic solvents; and the like.

Examples of pollutants reported to have reproductive and endocrine-disrupting effects include: organohalogens such as dioxins and furans, polychlorinated biphenyls (PCBs), polybrominated biphenyls (PBBs), octachlorostyrene, hexachlorobenzene, and pentachlorophenol; pesticides such as 2,4,5-T, 2,4-dichlorophenoxyacetic acid (2,4-D), alachlor, aldicarb, amitrole, atrazine, benomyl, beta-HCH, carbaryl, chlordane, cypermethrin, 1,2,dibromo-3-chloropropane (DBCP), dichlorodiphenyl trichloroethane (DDT), DDT metabolites such as dichlorodiphenyldichloroethane (DDD), dicofol, dieldrin, endosulfan, esfenvalerate, ethylparathion, fenvalerate, lindane, heptachlor, h-epoxide, kelthane, kepone (chlordecone), malathion, mancozeb, maneb, methomyl, methoxychlor, metiram, metribuzin, mirex, nitrofen, oxychlordane, permethrin, synthetic, pyrethorids, toxaphene, transnonachlor, tributyltin oxide, trifluralin, vinclozolin, zineb, and ziram; penta- to nonyl-phenols; bisphenol A; phthalates such as di-ethylhexl phthalate (DEHP), butyl benzyl phthalate (BBP), di-n-butyl phthalate (DBP), di-n-pentyl phthalate (DPP), di-hexl phthalate (DHP), di-propyl phthalate (DprP), dicyclohexyl phthalate (DCHP), and diethyl phthalate (DEP); styrene dimers and trimers; benzo (a) pyrene; and heavy metals such as cadmium, lead and mercury. Examples of pollutants reported to bind to hormone receptors and, accordingly, have potential reproductive and endocrine-disrupting effects include: 2, 4-dichlorophenol, diethylhexl adipate, benzophenone, n-butyl benzene, and 4-nitrotoluene. Other known or potential endocrine disrupters include: estradiol, diethylstilbestrol (DES), 1-hydroxychlordene, zearalenone, coumestrol, nonylphenol, butylphenol, pentylphenol, isopentylphenol, chlorpyrifos, pentachlorophenol (PCP), or derivatives thereof (See, Colborn et al., "Developmental Effects of Endocrine-Disrupting Chemicals in Wildlife and Humans," *Environmental and Health Perspectives* 101(5): 378–384 (1993).

The bioassay can be provided in a kit form that includes, in association, for example, containers for the test sample(s) and controls; a pipette or other like device for manipulating the Daphnia (test organisms); a sieve or other straining device for removing the Daphnia from the containers; a shallow glass dish or other like container for observing the Daphnia, a starter culture of a Daphnia clone as the test organism; directions for Daphnia culture; a starter culture of algal food species; directions for culturing the algae; a growth medium for culturing the Daphnia and/or the algae; directions for setting up and performing the bioassay; directions for scoring the results of test and model data scoring sheet; directions for statistical analysis of the results; software for data analysis; instructional video; information on standard responses of the Daphnia to known endocrine disrupters; a light source for altering the photoperiod during the assay; timer to regulate the light source for varying the photoperiod; or any combination thereof. The parts of the kit can be contained or separately packaged, for example, in a box or bag, and sold and distributed to users. The directions can be provided as a paper copy or on computer disk.

The invention will be further described by reference to the following detailed examples, wherein the methodologies are described below. These examples are not meant to limit the scope of the invention that has been set forth in the foregoing description. Variation within the concepts of the invention are apparent to those skilled in the art. The disclosures of the cited references throughout the application are incorporated by reference herein.

EXAMPLE 1

Minimal Growth Medium

The test sample(s) and control include a growth medium to provide minimal amounts of nutrients and trace elements and an algae food source for supporting the Daphnia neonates and offspring during the test period.

It is preferred that the growth medium is changed periodically during the test period in order to maintain sufficient food and oxygen concentrations, to remove neonates that began their development before the assay began (developmental time of the Daphnia eggs in the brood chamber is about 3–5 days), and to insure that the neonates scored at the end of the bioassay experienced their full development in the control and treatment solutions. It is also desirable to monitor the pH, conductivity and dissolved oxygen (DO) when the medium is changed to assure consistent conditions throughout the test period. Preferably, the growth medium is changed every 3–4 days during the test period. For example, for a 6–7 day assay, the growth medium is preferably changed at day 3–4.

A preferred growth medium is that developed by S. Kilham and C. Goulden (personal communication) which is prepared as follows. For one (1) liter of minimal growth medium, 1-ml of each of the Seven Major Stock Solutions, 1-ml of Algae Trace Elements Master Stock, 1-ml of Animal Trace Elements Master Stock, and 0.5 ml of Vitamin Master Stock are combined, and brought to a final volume of one (1) liter. Seven Major Stock Solutions. The following seven (7) major stock solutions are prepared separately by combining the listed salts in one (1) liter distilled water. The stock solutions are stored at room temperature):

| | | |
|---|---|---|
| 1) $CaCl_2.2H_2O$ | 36.76 g | calcium chloride dihydrate |
| 2) $MgSO_4.7H_2O$ | 36.97 g | magnesium sulfate heptahydrate |
| 3) $K_2HPO_4$ | 8.71 g | potassium phosphate dibasic anhydrous |
| 4) $NaNO_3$ | 85.01 g | sodium nitrate |
| 5) $NaHCO_3$ | 12.60 g | sodium bicarbonate |
| 6) $Na_2SiO_3.9H_2O$ | 24.42 g | sodium metasilicate nonanhydrate |
| 7) $H_3BO_3$ | 24.0 g | boric acid |

Algae Trace Elements Stock Solution. Mini stock solutions, each 100-ml in total volume, are prepared separately to contain one of the following salts. The solutions are refrigerated).

| | | |
|---|---|---|
| 1) $MnCl_2.4H_2O$ | 18.0 g | manganese(II) chloride tetrahydrate |
| 2) $CuSO_4.5H_2O$ | 0.1 g | copper(II) sulfate pentahydrate |
| 3) $ZnSO_4$ | 2.2 g | zinc sulfate heptahydrate |
| 4) $CoCl_2.6H_2O$ | 1.0 g | cobalt(II) chloride hexahydrate |
| 5) $Na_2MoO_4.2H_2O$ | 2.2 g | sodium molybdate dihydrate |
| 6) $H_2SeO_3$ | 0.16 g | selenious acid |
| 7) $Na_3VO_4$ | 0.18 g | sodium orthovanadate |

One (1) liter of Algae Trace Elements Master Stock Solution is prepared by combining the following ingredients. The EDTA is dissolved first to avoid formation of an insoluble precipitant:

| | | |
|---|---|---|
| 1) $Na_2EDTA.2H_2O$ | 4.36 g | ethylenediaminetraacetic acid, disodium salt dihydrate |
| 2) $FeCl_3.6H_2O$ | 1.0 g | iron(III) chloride hexahydrate |
| 3) 1-ml of each of the mini stock solutions (1–7). | | |

Animal Trace Elements. Mini stock solutions, each 100-ml in total volume, are prepared separately to contain one of the following salts. The solutions are refrigerated). One (1) liter of Animal Trace Elements Master Stock Solution is prepared by combining 1-ml of each of the mini stock solutions.

| 1) LiCl | 31 g | lithium chloride anhydrous |
|---|---|---|
| 2) RbCl | 7 g | rubidium chloride |
| 3) $SrCl_2 \cdot 6H_2O$ | 15 g | strontium chloride hexahydrate |
| 4) NaBr | 1.6 g | sodium bromide |
| 5) KI | 0.33 g | potassium iodide |

Vitamins Stock Solution. Mini stock solutions are prepared for the following two vitamins. The solutions are kept sterile and frozen:

| 1) biotin | dissolve 10 mg in 96-ml of $H_2O$ |
|---|---|
| 2) $B_{12}$ | dissolve 10 mg in 89-ml of $H_2O$ |

A Vitamin Master Stock Solution of 100-ml total volume is prepared by adding 1-ml of each of the biotin and $B_{12}$ stock solutions, and 20-mg thiamine. The master stock solution is dispensed into 10-ml lots and autoclaved or microwaved.

EXAMPLE 2

Bioassay of Two Pesticides for Activity as an Endocrine Disrupter

Two widely used contemporary pesticides, dieldrin and endosulfan, were tested for activity as endocrine disrupters using the present Daphnia reproduction bioassay.

Levels of exposure of the pesticides were chosen based on reports of results of standard bioassays (for fecundity and survivorship) in the literature. Concentrations were chosen that were at or below levels known to have toxic effects in Daphnia or other freshwater species. Concentrations of 10 and 100 µg per liter of each pesticide alone, and a mixture of the two pesticides, both at either 10 and 100 µg per liter.

The bioassay was performed as follows. The experimental unit was a glass jar containing 30-ml of the growth medium described in Example 1 above, and a 1:1 mixture of the green algae, *Chlamydomonas reinhardti* and *Selenastrum capricornutum* (Culture Collection & Algae, Department of Botany, University of Texas at Austin, Austin, Tex. 78713-7640) which provided the algal mixture at an initial level of about 5×105 cells per ml (about 6.9 mg carbon per ml). Into each jar were placed three (3) adult egg-carrying female Daphnia galeata mendotae Wingra CDF-1 clone (University of Wisconsin-Madison, Department of Zoology). The Daphnia were incubated in an environmentally-controlled chamber for three (3) days at 20° C. and 9 hours of light (500 µE per meter squared per second (maximum) per day . Each jar contained growth medium with or without additional chemical, as shown below. Each Control or treatment was replicated 15 times.

Controls:

| Control: | Growth medium, algae |
|---|---|
| Acetone Control: | Growth medium, algae, 200 mg/L Acetone |

Treatments: Growth medium, algae, plus:

| Low Dieldrin Treatment: | 10 µg/l Dieldrin |
|---|---|
| Low Endosulfan Treatment: | 10 µg/l Endosulfan |
| Low Mixture: | 10 µg/l Dieldrin, 10 µg/l Endosulfan |
| High Dieldrin Treatment: | 100 µg/l Dieldrin |
| High Endosulfan Treatment: | 100 µg/l Dieldrin |
| High Mixture: | 100 µg/l Dieldrin and 100 µg/l Endosulfan |

At the end of three (3) days, the adults were pipetted into new jars containing 30-ml of fresh growth medium and algae food source, and any neonates were discarded. After another three (3) days, the neonates and adults in the bottle were counted and scored for survivorship, resting eggs, and gender.

Results of the experiments with low concentrations of pesticides showed no difference in survivorship, fecundity, resting eggs, or gender between the two controls or between the controls and any of the treatments.

Results of the experiments with low levels of pesticides are shown below in Table 1.

TABLE 1

| TREATMENTS | NUMBER OF FEMALES | NUMBER OF MALES |
|---|---|---|
| Control | 146 | 18 |
| Acetone Control | 143 | 17 |
| Low Dieldrin | 144 | 21 |
| Low Endosulfan | 151 | 22 |
| Low Dieldrin and Low Endosulfan | 132 | 21 |

Results of the experiments with high levels of pesticides for the first clutch are shown below in Table 2.

TABLE 2

| TREATMENTS | NUMBER OF FEMALES | NUMBER OF MALES |
|---|---|---|
| Control | | |
| Acetone Control | 114 | 13 |
| High Dieldrin | | |
| High Endosulfan | | |
| High Dieldrin and High Endosulfan | 65 (10 replicates) | 14 |

Results of the experiments with high levels of pesticides for the second clutch are shown below in Table 3, and illustrated in FIG. 1.

TABLE 3

| TREATMENTS | NUMBER OF FEMALES | NUMBER OF MALES |
|---|---|---|
| Control | 118 | 18 |
| Acetone Control | 116 | 13 |
| High Dieldrin | 120 | 14 |
| High Endosulfan | 126 | 8 |
| High Dieldrin and High Endosulfan | 121 | 3 |

The results of the experiments with high level of pesticides showed no difference between the two controls, no difference between the controls and the dieldrin treatment, a tendency for a reduction of males in the endosulfan treatment but no other changes, a strong reduction in sex ratio (few males) in the mixture, and a slight (not significant) adult mortality (12%). These results indicate that endocrine disruption occurred at levels below those that are lethal or even affect fecundity or survivorship, and a synergistic interaction of the two pesticides.

EXAMPLE 3

Method and Protocol for Daphnia Reproductive Bioassay for Testing an Aqueous Sample To test a water sample for a biologically-active level of a toxic chemical and/or the presence of a chemical substance that functions as an endocrine disrupter, the Daphnia reproductive bioassay can be run as follows.

A series of test sample and control experimental units can be prepared and the bioassay run under the conditions described in Example 2. The control and test samples can be replicated so there are multiple units that are assayed for each. The unknown water sample can also be run as serial dilutions by adding a range of amounts of the water sample to the growth medium, for example from 1–15 ml of the water sample with 0.9–15 ml growth medium. The control is made with the minimal growth medium but with no added water sample.

After three (3) days, the adults are transferred to fresh growth medium and the neonates removed. After an additional three days, the neonates and adults in each experimental unit are scored for survivorship, resting eggs and gender, and the 5 parameters scored and compared between test samples and control.

EXAMPLE 4

Sublethal Toxic Effects of Cyanobacteria and Nonylphenol on Environmental Sex Determination and Development in Daphnia The effects of toxic stress were studied on *Daphnia galeata-mendotae* grown under conditions in which the organism produces female, male and ephippial offspring (Shurin, J. and S. I. Dodson, "Sublethal toxic effects of Cyanobacteria and nonylphenol on environmental sex determination and development in Daphnia," *SETAC Journal* (in press, 1997). The bioassay used was a 21-day protocol that started with Daphnia neonates. Fecundities in terms of three (3) types of offspring showed different sensitivities to chemical stress. The toxic agents were a natural toxin produced by a toxic strain of the cyanobacterium *Microcystis aeruginosa,* and an anthropogenic toxin, a chemical plasticizer nonylphenol which is a surfactant that interferes with endocrine function in vertebrates.

Production of resting egg and female offspring were affected in both cases, but showed different dose responses. Exposure to nonylphenol also produced a characteristic developmental abnormality at environmentally relevant concentrations. Some neonates that were prenatally exposed to toxins showed signs of incomplete morphological transition from embryo to juvenile. Life table analysis showed stress during the sexual phase of Daphnia's life cycle reduced population growth.

The cyanobacterium, *Microcystis aeruginosa* produces chemical defenses against grazing by herbivorous zooplankton and often forms large toxic blooms especially in eutrophic lakes. Microcystis suppresses growth and reproduction of grazers in three ways: by producing toxins, by forming gelatinous aggregates that interfere with filtering appendages, and by providing low nutritive value.

Nonylphenol is a prevalent surfactant in sewage effluents. Nonylphenol and its ethoxylate derivatives have been detected at levels up to 330 and 419 $\mu g \cdot L^{-1}$ in British and Swedish waste waters respectively, and at 1.3 to 180 $\mu g \cdot L^{-1}$ in river waters in the same studies. Chronic $LC_{50}$ values for *D. magna* of 120, 120 and 100 $\mu g \cdot L^{-1}$ have been found in 7-, 14- and 21-day tests, respectively. Concentrations in waters show considerable variation in time and space, indicating that nonylphenol can be rare but present at biologically significant levels. Nonylphenol bioaccumulates in tissues, so effective exposure levels increase with time of contact. Nonylphenol and its derivatives have been shown to be estrogenic to fish, mammals and birds.

Life table analysis. Data from the Microcystis and nonylphenol experiments were analyzed to determine the consequences for short-term population dynamics of chemical stress on Daphnia in the initial stage of sexual reproduction. The instantaneous rate of population increase (r) was estimated for experimental animals grown at different levels of toxic stress. The rate of increase is a measure of the growth rate of the population of live, pelagic females available for immediate sexual or asexual reproduction. It is a function of survival and fecundity of animals of different age classes. Toxins that affect r can influence population dynamics over multiple generations, even if actual exposure takes place during only one generation. The rate of increase only considers present production of female animals and does not take into account multi-generational effects that may occur from reduced ephippia production.

Methods

General Methods for Bioassay. The animals used were a single clone (CDF-1) of *Daphnia galeata-mendotae* collected from Lake Wingra, Wis., USA by Thomas O'Keefe in December, 1994. This clone produces female, male and ephippial offspring when crowded. Several generations were grown in the lab before the experiment. Pairs of neonates (<36 hours old) were placed into 30-ml of medium at the beginning of the study. Animals were grown in pairs to provide crowding as a stimulus for the production of males and ephippia. The experiment began with sixteen replicate jars, and jars were discarded if either animal died.

The medium was changed and the containers rinsed with distilled water every 2 days. Male, female and ephippial offspring were counted by visual inspection (at 25×) on days when the medium was changed and any mortality among the parental Daphnia was recorded. The medium in which the algae and zooplankton were cultured was the combination formula as described hereinabove in Example 1. This formula eliminates the problem of mineral rich algal culture medium causing unwanted effects on Daphnia. The zooplankton medium was kept under constant vigorous aeration before being used. Animals were grown in an environmental chamber at 20° C. with a constant 9:15 hour light:dark photoperiod. These conditions are similar to those during fall in Wisconsin when *Daphnia galeata-mendotae* undergo sexual reproduction.

Microcystis experiment. Semi-continuous cultures of the green alga *Chlamydomonas rheinhardii* (UTEX 90) and the cyanobacterium *Microcystis aeruginosa* (UTEX LB 2385) in log-phase growth provided food for zooplankton. Treatment levels were four ratios (by total particulate carbon content) of *Microcystis:Chlamydomonas:* 0:1, 1:9, 1:3, and 1:1. The strain of Microcystis that was used produces the toxin microcystin.

Animals were fed a total of 0.6 mg $C-L^{-1}$ (in particulate organic carbon) at the beginning of the experiment. After low reproduction in the first clutch, the food was increased to 1.0 mg $C-L^{-1}$ on the 10th day. Algae were added to the zooplankton medium immediately before the medium was introduced into the experimental containers. Concentrations of cells in the algae cultures were determined spectroscopically from standardized absorption curves. Carbon content of Microcystis was determined as described by W. Lampert, "Inhibitory and toxic effects of blue-green algae on Daphnia", *Int. Revue ges Hydrobiol.* 66(3):285–298 (1981). The containers were gently agitated on the days when the medium was not changed to resuspend any algal cells that had settled. The experiment was ended after 36 days.

Nonilphenol Experiment. Medium and growing conditions were the same as in the Microcystis experiment. Animals were fed 1 mg C-L$^{-1}$ Chlamydomonas which was increased to 1.2 mg C-L$^{-1}$ on the 6th day of the experiment because of poor growth. Three concentrations of nonylphenol were tested, 10, 50 and 100 $\mu$g-L$^{-1}$. In a preliminary experiment 100% mortality among animals was observed at 150 $\mu$g-L$^{-1}$ over 48 hours. Nonylphenol was dissolved in an acetone carrier to enhance its solubility in water. Carrier effects were tested by running controls with and without acetone. In the acetone control and in all the nonylphenol treatments, the acetone concentration was kept constant at 80 $\mu$g-L$^{-1}$. Stock solutions of chemicals for each treatment were kept refrigerated and added to the zooplankton medium immediately before it was used in the experimental containers. The experiment was ended after 30 days because of low survival in the 100 $\mu$g-L$^{-1}$ nonylphenol treatment and reduced reproduction in all treatments.

Some five offspring in the nonylphenol treatments showed developmental abnormalities. These offspring were approximately the same size as normal young but had forward-curled tail spines (a characteristic of Daphnia in embryonic stages) and lacked or had severely reduced terminal setae on their second antennae. These setae are used for swimming and deformed animals were unable to move or attempt to escape capture by a pipette. Offspring were considered to be deformed if they exhibited both a bent tail spine and reduced or absent terminal setae. All deformed offspring were assumed to be inviable and were not included in estimates of r. Deformed young were counted in calculating production of male and female offspring. Deformed offspring were not observed in the medium or solvent controls or in the Microcystis experiment.

Life table analysis. The average instantaneous rate of increase (r) and confidence intervals were calculated for each treatment by the Jackknife method described by Meyer et al., *Ecology* 67(5):1156–1166 (1986), and the Jackknife pseudovalues were included in the statistical analysis. All jars initiated at the beginning of the experiment were included in estimates of r. When an animal died, its partner in the jar was removed from the pool used to calculate the survivorship function ($l_x$). This was done by subtracting one animal (the dead Daphnia) from the number surviving on the day that the animal died. The other animal (the survivor) was subtracted from the total number possible (the denominator in $l_x$) on the next sampling point two days later. This correction prevented mortality estimates from being inflated by animals that were discarded but did not die.

Statistical analysis. Each jar with 2 adults was considered an experimental replicate in data analysis. Dependent variables were numbers of female, male, deformed and ephippial offspring per adult female per day (number•female$^{-1}$•day$^{-1}$) and the Jackknife pseudovalues of r. Effects of treatment level were analyzed by ANCOVA with longevity as a covariate. ANCOVA allowed the separation of the portions of the observed effects into two parts: that which was due to treatment, and that which was due to differences in longevity. Since Daphnia tend to produce ephippia in later clutches, decreases in average daily production of ephippia can be attributed to early mortality or lower output. The production of females, males, ephippia and deformed offspring for replicates that produced at least one clutch, and r for all replicates were analyzed. All analyses were done with the SYSTAT version 5.0 statistical package (SYSTAT for Windows: DATA, Version 5 Edition, 187 pp., Evanston, Ill., SYSTAT, Inc. (1992).

Results

Microcystis experiment. The results of the Microcystis experiment are shown in FIG. 2. No significant differences in production of offspring for animals grown with less than 25 % Microcystis in their diets was found. Between 25% and 50% Microcystis, daily ephippia production decreased by two thirds (FIG. 2*a*).

Results of the ANCOVA shown below in Table 4 indicate that longevity did not play a large role in the effect on ephippia production, and the decrease was therefore attributed to an actual reduction in average daily output. Numbers of female offspring decreased in a step fashion from 25% to 50% Microcystis (FIG. 2*b*) and male offspring were not affected at any level (FIG. 2*c*). Longevity explained a large part of the reduction in production of female offspring (Table 4). The effect of increasing concentrations of Microcystis on ephippia production was considerably more dramatic than on either male or female production.

TABLE 4[1]

| Dependent Variable | Source | df | ss | ms | F | P |
|---|---|---|---|---|---|---|
| Females | Treatment | 3 | .015 | .005 | 1.367 | .265 |
| n = 51 | Longevity | 1 | .030 | .030 | 8.182 | *.006* |
| Males | Treatment | 3 | .003 | .001 | 1.245 | .304 |
| n = 51 | Longevity | 1 | .000 | .000 | .042 | .838 |
| Ephippia | Treatment | 3 | .008 | .003 | 3.019 | *.039* |
| n = 51 | Longevity | 1 | .002 | .002 | 2.483 | *.122* |
| r | Treatment | 3 | .001 | .000 | .315 | .815 |
| n = 60 | Longevity | 1 | .008 | .008 | 5.01 | .030 |

[1]P values of variables for which the data violate the assumption of normality are italicized.

The assumption of normality was tested by a Lillefiore's test and significant departures in production of females and ephippia were found. The assumption of homogeneity of variance was tested by dividing the largest sample variance by the smallest; it did not exceed 9 in any case. ANCOVA is robust to such violations of assumptions (J. F. Zolman, *Biostatistics,* Oxford University Press, Oxford, U.K. (1993).

Nonylphenol experiment. Microcystis and nonylphenol produced qualitatively different results, as shown in FIG. 3. A clear dose response to nonylphenol was seen in the production of deformed live offspring (P<0.001; FIG. 3*a*).

Results of the ANCOVA shown below in Table 5 indicate that the effect on deformed offspring was not a product of reduced longevity. Daily production of females increased at high dosages and in the presence of the acetone solvent (FIG. 3*b*). Reductions in r and in ephippia production were largely a result of increased adult mortality (FIG. 3*c* and *d;* Table 5). Numbers of male offspring were not affected at any level (FIG. 3*e*). The inverse dose response to nonylphenol in female production was unexpected, however the strongly linear pattern in deformed offspring with respect to dose lends confidence that exposure levels were reliable.

TABLE 5

| Dependent Variable | Source | df | ss | ms | F | P |
|---|---|---|---|---|---|---|
| Females | Treatment | 4 | .024 | .006 | 3.700 | *.011* |
| n = 49 | Longevity | 1 | .002 | .002 | 1.273 | .265 |
| Males | Treatment | 4 | .002 | .000 | .899 | .473 |
| n = 49 | Longevity | 1 | .000 | .000 | .108 | *.744* |
| Ephippia | Treatment | 4 | .007 | .002 | 2.340 | .070 |
| n = 49 | Longevity | 1 | .005 | .005 | 6.986 | *.011* |
| Deformed | Treatment | 4 | .018 | .005 | 18.115 | .000 |
| n = 49 | Longevity | 1 | .001 | .001 | 3.190 | *.081* |
| r | Treatment | 4 | .007 | .002 | 3.168 | *.019* |
| n = 78 | Longevity | 1 | .067 | .067 | 119.18 | .000 |

[1]P values of variables for which the data violate the assumption of normality are italicized.

Life table results. Population growth rates differed among treatments in both experiments. r decreased steadily with increasing concentration of Microcystis (FIG. 2d). In the nonylphenol experiment, r was predictably sensitive to production of female offspring and showed a nonlinear pattern (FIG. 3c). No correlation was found between the Jackknife pseudovalues of r and production of deformed neonates (Kendall's rank coefficient of correlation, τ=−0.057, P>0.1). Therefore, the decrease in r was not a product of the omission of deformed offspring.

Decreases in male and female production and in r in the medium control of the nonylphenol experiment compared to the Microcystis experiment was observed despite nearly identical growing conditions (the food level was slightly higher in the nonylphenol experiment, see Methods). FIG. 4 illustrates that both survivorship and fecundity were lower in the nonylphenol experiment than the Microcystis experiment. Therefore, both contributed to lower r in the nonylphenol experiment control.

Discussion

As shown in this assay, chemical stress can have complex effects on Daphnia populations that undergo periodic sexual reproduction. Production of males, females and ephippia were sensitive to different levels of contamination and were affected both by changes in average daily output and by shorter life spans of the animals. The two stressors, Microcystis and nonylphenol, affected *Daphnia galeata-mendotae's* production of females, males and ephippia in different ways. Changes in the abundances of each of the three reproductive forms of Daphnia will have unique effects on a population's growth and persistence.

Microcystis. In the presence of cyanobacteria, there is an increase in production of ephippia and a decrease in fecundity in female offspring. The results show that Daphnia's ability to produce ephippia will be limited if the sexual phase of Daphnia's life cycle takes place under severe stress from cyanobacteria. Reduced production by females and depressed population growth rate, r, both result in a lower supply of ephippia to the resting egg bank. The levels of Microcystis used were environmentally realistic for a eutrophic lake. The biovolume of Microcystis in the highest treatment level (4.55 $\mu$L-L$^{-1}$) was in the range (2–17 $\mu$L-L$^{-1}$) observed on 4% of sampling dates in Lake Mendota, Wisconsin from 1976–89. However, cyanobacteria as a group were present at >2 $\mu$L-L$^{-1}$ on 16% of sampling dates from the same period, and reached a maximum concentration of 17 $\mu$L-L$^{-1}$. This indicates that Daphnia are likely to encounter cyanobacteria at levels that inhibit ephippia production.

A dramatic decrease in ephippia output at 50% Microcystis was observed (FIG. 2c). Growing conditions were chosen for maximal induction of males and ephippia, and the clone that was used may have been unable to allocate further effort to ephippia. Although under some conditions Daphnia increase ephippia production when exposed to stress from cyanobacteria, when conditions favor production of males and ephippia (short day length, low food, high densities of animals), ephippia are more heavily reduced than live young by toxic chemical defenses.

Nonylphenol. High doses of nonylphenol increased female offspring production while numbers of ephippia decreased slightly and male production remained constant. The solvent control (80 $\mu$g-L$^{-1}$ acetone) showed greater production of female offspring than the medium control (FIG. 3b). This was due to sensitivity of the clone to acetone, and/or a heightened sensitivity to nonylphenol or its interaction with acetone due to exposure to sex-inducing environmental stresses.

There was a lack of pattern for female production with respect to dose of nonylphenol. First, the difference between the medium and solvent controls indicates that the effect of acetone was not negligible and that an interaction between dose of nonylphenol and acetone may have been important. Second, inverse dose responses characterize the activity of some chemicals, such as endocrine disrupters, which can interact with multiple physiological processes. The mechanism of activity of chemicals such as nonylphenol that affect endocrine function changes with exposure levels, causing one biological effect to be replaced by another as dose increases. The pattern for female offspring production and the deformity associated with nonylphenol indicates that direct chemical interactions with developmental processes occur in Daphnia, as well as in a wide range of vertebrates.

Development. Prenatal exposure to nonylphenol caused a nonlethal but disabling abnormality at the stage where Daphnia develop from embryos into juveniles. The deformity was seen in 11% of live young grown at 10 $\mu$gL-L$^{-1}$ nonylphenol, below the "no-observed effect concentration" (NOEC) of nonylphenol for *D. magna* of 24 $\mu$gL-L$^{-1}$ and within the range commonly found in waters that receive sewage effluent. Only animals that were prenatally exposed to nonylphenol exhibited the deformity, indicating that Daphnia are especially vulnerable to chemical interference at early developmental stages. Nonylphenol consistently affected morphological development of tail spines and swimming setae, suggesting that its activity involves specific ontogenetic processes.

Life tables. Short term population dynamics of asexual females were affected by exposure to both Microcystis and nonylphenol. Depression of r lowers the population of adults that can contribute ephippia and can affect trophic interactions with Daphnia's resources and consumers. The two experiments illustrate that effects on r occur independently of effects on male and ephippial young.

EXAMPLE 5

Effect of Dieldrin and Endosulfan on Male Production and Sex Ratio in Daphnia Galeata The following bioassay was conducted to determine the effect of chemicals known to be endocrine disrupters in vertebrates on the morphogenesis or reproduction in Daphnia. The bioassay was designed to clarify the action of exogenous agents that were suspected of being able to interfere with normal reproduction and development in Daphnia, that is, chemicals that act like endocrine disrupters. Two insecticides known to be weakly estrogenic in vertebrate systems were used: endosulfan and dieldrin. The treatments were designed to allow detection of non-additive effects of a mixture of the two pesticides and the possible synergistic effects of the two environmental contaminants.

The sex ratio of neonate Daphnia was used as an endpoint for detecting morphological and developmental effects of the insecticides endosulfan and dieldrin. A 6-day bioassay was run, and the endpoints that were measured included: adult survivorship and fecundity, neonatal sex ratio, and morphology. Dieldrin caused a decrease in sex ratio. No endosulfan effect was observed. The sex ratio was reduced by dieldrin down to a concentration of about 30 pph based on a linear decrease in sex ratio with log dieldrin concentration from 50 and 600 ppb. Neither insecticide significantly affected adult survival or clutch size. Because sex ratio changed but total neonate production did not change, the data indicate that the effect of dieldrin was on the sex-determining system during embryogenesis. Neither insecticide caused morphological abnormalities. Mixtures of the two pesticides produced additive effects.

Materials and Methods

The reproduction bioassay test animal was the CDF-1 clone of *Daphnia galeata mendotae* collected from Lake Wingra, Wis., December 1994. Daphnia were exposed to contaminants during embryogenesis, the life history stage during which they are particularly sensitive to contaminants and a developmental period that is generally important for endocrine disruption. Abnormal morphological development of the newly born males and females may also be observed. Under the correct environmental conditions, natural environmental signals cause males to be produced in lake populations: adult Daphnia females are typically crowded together and experience short day lengths of about LD 9:15. The bioassays were kept as 21° C. At temperatures higher than about 23° C., there was increasing mortality, and at lower temperatures, the animals took much longer to develop. Under the "control" conditions, mortality was consistently low and the reproduction rate and sex ratio were high enough to test for shifts in sex ratio of roughly 10–15%.

The experimental unit was comprised of three or four adult egg-carrying female Daphnia placed together into a 50 ml glass jar containing 30 ml of artificial ("combo") lake water medium. Combo medium, designed by Clyde Goulden and Susan Kilham, was used both to grow algae and to culture Daphnia (See Example 1). This medium has an electrical conductance of about 240 $\mu$mhos and a pH of about 8.4.

The density of three adults in 30 ml provides "crowding" for the induction of males. In the later bioassays, the number of adults per jar was increased to four, in order to produce a higher level of male production in the control treatments.

Each jar contained approximately equal numbers of the algae Chlamydomonas and Selenastrum for food to produce a suspension of $5 \times 10^5$ cells ml$^{-1}$. Although the algae sediments out of the small (short) jars, and the Daphnia experience a variation in food concentration from $5 \times 10^5$ cells ml$^{-1}$ to near zero, there was adequate food for the Daphnia to maintain reproduction.

A minimum of ten jars were used per treatment. Treatments include 1) a "control" made with "combo" medium but with no added chemical or suspect water, and 2) a control treatment including the carrier used in the bioassay (acetone) at the highest concentration used in any treatment in that experiment, and 3) chemical exposure treatments made with "combo" medium, algae, and dilutions of the chemical to be tested (along with its acetone carrier). The higher acetone concentration used (60 uL acetone L$^{-1}$) is less than 0.01 % of the 16-day growth NOEC and less than 0.5% of the LC$_{50}$ for survival or LOEC for reproduction for *Daphnia magna* in the 3-brood test.

The concentrations of endosulfan and dieldrin (Chem Service, West Chester, Pa.) were between 50 and 600 ppb, near or below concentrations known to affect survival or fecundity. For example, endosulfan affects Daphnia population growth at about 120 ppb, and reduces filtration and assimilation rates at about 440–600 ppb (Fernandez-Casalderrey et al., *Comp. Biochem. Physiol. C. Comp. Pharmacol. Toxicol.* 106:437–441 (1993); Fernandez-Casalderry et al., *Ecotoxicol. and Environ. Safety* 27:82–89 (1994)). Long-term exposure to endosulfan reduces Daphnia carinata body length and weight, reduces egg mass and brood size between 40 and 160 ppb, and delays time of first reproduction at 440 ppb. Endosulfan treatment did not induce changes in relative allocation of available resources for reproduction. A long-term life table study of dieldrin found that had little or no effect on population growth rate below about 220 ppb (Daniels et al., *Can. J. Fish. Ag. Sciences* 38:405–494 (1981)). Clearly, if the pesticide is at high enough concentrations to see reduced fecundity or reduced survivorship, then there is less chance of seeing a subtler shift in male production or sex ratio.

The design of the five bioassays is shown in Table 6, below. The bioassays were designed to test for synergistic effects of the two pesticides.

TABLE 6

| Bioassay | Treatments (Concentrations are in $\mu$g liter$^{-1}$, except for acetone, which is in units of TL L$^{-1}$) All bioassays included an additional "water" control that lacked additional chemicals. | No. of Replicates | Adults jar$^{-1}$ |
|---|---|---|---|
| 1. | Acetone (20 TL L$^{-1}$), Endosulfan (50), Dieldrin (50), Mixture (50 + 50) | 15 | 3 |
| 2. | Acetone (20 TL L$^{-1}$), Endosulfan (100), Dieldrin (100), Mixture (200 + 200) | 10 | 4 |
| 3. | Acetone (20 TL L$^{-1}$), Endosulfan (200), Dieldrin (200), Mixture (200 + 200) | 10 | 4 |
| 4. | Acetone (60 TL L$^{-1}$), Endosulfan (100, 200, 400, 600) | 13 | 4 |
| 5. | Acetone (60 TL L$^{-1}$), Dieldrin (100, 200, 400, 600) | 14 | 4 |

The adult Daphnia were incubated for 3 days, about the length of one molt cycle (neonates are released each time the adult molts). At the end of the 3 days, the adults were transferred to new medium and the first batch of young were discarded. The rational for the transfer is that the first batch of young were not all exposed to the test chemicals for the entire developmental period. It is likely that some adults molted and released young as soon as they were placed in the jars. However, any young released after the first three days would have spent their entire developmental period exposed to their parent's treatment solution. Moving adults to new medium also allows for renewing the algae supply.

After an additional three days, the contents of each jar were poured into a petri dish, the water was removed with a pipette, and the number of adults, resting eggs, and newborn males and females were scored using a low-magnification dissecting microscope. The following five endpoints were measured. Morphological structures were assessed based on the illustrations in J. L. Brooks, *The Systematics of N. A. Daphnia, Memoirs of Conn. Academy of Arts and Sciences,* Vol. 23 (1957).

1) Number of adult females that survive 6 days. This is about 75–100% in all treatments because endocrine-disruption is expressed at sub-lethal concentrations of chemicals.

2) Number of neonates produced per female during the last 3 days of the assay. Neonates were scored separately as males and females.

3) Sex ratio based on number of male and female neonates produced during the last 3 days of the assay.

4) Number of resting eggs produced during the last 3 days of the assay.

5) Developmental abnormalities in the neonates.

Acceptance Criteria. The bioassay data was reviewed based on the following criteria to determine whether the data was adequate to complete the analysis. If not, the analysis was not completed. The bioassay data of the present experiment was acceptable if, at the end of 6 days:

1. For each treatment, there was at least 8 replicates containing at least 3 neonates in each replicate. Replicates with 2 or fewer neonates were not included in the statistical analysis.

2. The adult females showed at least 70% survival, averaged over the two control treatments. Normal aging of adults typically produces a survivorship of about 70–95% for the 6 day assay period.

3. The water and acetone (carrier) controls did not have significantly different sex ratios within the experiment.

4. The average sex ratio in the combined controls were at least 10% males in order to allow statistical detection of a significant decrease in males.

Data Analysis Protocol. For each experimental unit (a single jar), at the end of the 6 days, the number of surviving adults, male and female neonates, number of ephippial eggs present, and any abnormal morphologies were recorded. The sex ratio was calculated as:

sex ratio=(number of males)/(number of males plus females)

Ten to fifteen sex ratio replicates were used for each control or treatment, depending on the specific bioassay (Table 7). The experimental design was to choose a concentration of dieldrin and endosulfan in the range of 50 to 600 ppb, and to expose Daphnia to the following treatments:

TABLE 7

|  | Dieldrin absent | Dieldrin present |
|---|---|---|
| Endosulfan absent | water and acetone controls | dieldrin effect |
| Endosulfan present | endosulfan effect | synergistic effect |

Based on the scoring of a preliminary bioassay (not included in the formal analysis), three endpoints were identified that showed a variation: sex ratio, adult survivorship, and neonates per adult. No morphological abnormalities were observed, although Daphnia are reported to show morphological changes at endosulfan concentrations as low as 0.1 $\mu gL^{-1}$. Number of ephippial eggs was not used as an endpoint because there were too few eggs to analyze.

Statistical Analysis. The first step in the statistical analysis was to conduct a t-test to determine whether the null hypothesis for each of the three endpoints separately could be rejected that the two controls (plain combo control and acetone carrier control) were significantly different. If the null hypothesis was not rejected at the 5% level (as was always the case), then the two controls were combined. Combining the controls has the advantage of increasing (doubling) the number of degrees of freedom for the pair-wise t-tests in which a treatment value is compared to a value, and for the within-groups sums of squares for the Anova tests, thereby increasing the sensitivity of the tests.

Each single-chemical treatment was compared to its proper control, using a t-test to calculate the one-tailed probability of the null hypothesis, given a) a decrease in sex ratio, b) a decrease in adult survival, and c) a decrease in neonates per adult. In order to understand the overall effect for each insecticide, the individual t-test probabilities were combined (Sokal et al., *Biometry* (2d ed.), NY: Freeman (1981). Sex ratio was arcsin transformed for statistical analysis. If the combined probability (for a given endpoint and insecticide) was significant at the 0.05 level for a given endpoint and insecticide, then a regression analysis was performed on the averages of the treatments and the logarithms of the insecticide concentrations. The regression was interpreted as a dose-response relationship.

Results were tested for significant interaction effects (within each bioassay) using 2-way Anova (Sokol (1981). A significant interaction term (endosulfan×dieldrin) is one indication of a significant synergistic effect.

Results

Three endpoints were focused on: sex ratio, total offspring production and adult survival. Water controls were not significantly different from the acetone controls in any of these bioassays (t-test, p>0.05) for any of the three tests were analyzed statistically. Therefore, the data in the two controls were combined for comparison with the results of the other treatments.

The first analysis was done by pair-wise t-tests, to determine whether there are significant affects of the chemicals on sex ratio, adult survival, or number of neonates produced per adult, as shown in Table 8, below. Table 8 shows the results of comparisons among treatments and controls for three different endpoints, in five bioassays. The sign of the probability indicates whether the treatment value for the endpoint was above or below the control level. The df for the combined probabilities=14; for interaction terms=1, and 50–90. Combined probabilities are calculated using the method by Fisher, cited in R. R. Sokol and F. J. Rohlf, *Biometry* (2d ed.), W. H. Freeman and Ca, N.Y., at page 780 (1981).

TABLE 8

|  | Bio-assay | ENDO-SULFAN | Bio-assay | DIELDRIN |
|---|---|---|---|---|
| SEX RATIO |  |  |  |  |
| t-test probability | 1 | −0.183 | 1 | +0.451 |
|  | 2 | −0.252 | 2 | −0.038 |
|  | 3 | −0.031 | 3 | −0.221 |
|  | 4 | +0.346 | 5 | −0.152 |
|  | 4 | +0.366 | 5 | +0.476 |
|  | 4 | +0.087 | 5 | −0.041 |
|  | 4 | −0.268 | 5 | −0.023 |
| combined probability (1-way) |  | p > 0.223 |  | p = 0.008 |
| Interaction probability | 1 | .356 |  |  |
|  | 2 | .810 |  |  |
|  | 3 | .262 |  |  |
| ADULT SURVIVAL |  |  |  |  |
| t-test probability | 1 | +0.309 | 1 | +0.393 |
|  | 2 | +0.158 | 2 | −0.459 |
|  | 3 | +0.0035 | 3 | −0.010 |
|  | 4 | +0.412 | 5 | −0.419 |
|  | 4 | −0.261 | 5 | −0.117 |
|  | 4 | +0.500 | 5 | −0.167 |
|  | 4 | +0.136 | 5 | −0.365 |

TABLE 8-continued

| | Bio-assay | ENDO-SULFAN | Bio-assay | DIELDRIN |
|---|---|---|---|---|
| combined probability (1-way) | | p = 0.321 | | p = 0.054 |
| interaction probability | 1 | .830 | | |
| | 2 | .690 | | |
| | 3 | .263 | | |
| NEONATES PER ADULT | | | | |
| t-test probability | 1 | +0.227 | 1 | −0.305 |
| | 2 | −0.230 | 2 | −0.498 |
| | 3 | +0.276 | 3 | +0.260 |
| | 4 | +0.116 | 5 | −0.074 |
| | 4 | +0.183 | 5 | +0.104 |
| | 4 | +0.203 | 5 | +0.192 |
| | 4 | +0.247 | 5 | +0.409 |
| combined probability (1-way) | | p = 0.0 | | p > 0.05 |
| interaction probability | 1 | .415 | | |
| | 2 | .824 | | |
| | 3 | .867 | | |

Sex ratio was decreased significantly in the dieldrin treatment. The change in sex ratio was graphed (FIG. 5) as the log dieldrin concentration vs. the sex ratio index.

The index was calculated as the difference between the control and the treatment sex ratio. For example, if the control sex ratio is 0.25 and the treatment ratio is 0.15, then the index is (0.25−0.15) or 0.10. Sex ratio index and log dieldrin concentrations were correlated using Spearman Rank Correlation ($n=7$, $r=0.73$, $p>0.05$). The Pearson Product-Moment linear correlation was nearly significant ($p=0.07$), and the regression line ($Y=-0.0195X+0.299$, where Y=sex ratio index and X=log ppb dieldrin) had the X intercept at 31 ppb.

The results showed no significant decrease in short-term adult survivorship or fecundity (number of offspring produced in the second half of the bioassay). These results indicate that the bioassays were performed at low pesticide concentrations.

It was not possible to reject the null hypothesis concerning the interaction of endosulfan and dieldrin (Table 8). Combining the interaction probabilities for the three 2-way Anovas did not produce a significant effect.

Discussion

Each year thousands of new organic chemicals are brought to the market place.

Typically, these chemicals are screened for acute toxicity and ability to cause cancer because of concern about wildlife and especially human health. However, many of these chemicals, including common industrial and agricultural chemicals, have additional effects of critical importance to wildlife and human health. These additional effects include interference with normal development, reproduction, and behavior of exposed individuals and their descendants and with normal biochemistry and growth. Chemicals are typically screened using either vertebrate (usually vertebrate) or molecular (usually human-derived) techniques. Vertebrate assays have the advantages of a whole-animal test using organisms relatively similar to humans. However, vertebrate assays are poorly suited for screening large numbers of chemicals because of their cost, complexity, and ethical concerns. Molecular assays provide a rapid screen for specific reactions or receptors. However, whole animal assays are preferable compared to molecular assays, when the concerns are with developmental and reproductive processes.

The arthropod Daphnia (water flea: Crustacea: Anomopoda) provides a simple animal model for screening for developmental and reproductive effect. Daphnia typically reproduce asexually, having only female offspring. Under certain natural conditions (and the bioassay conditions), Daphnia reproduce sexually and produce males and haploid eggs. Males are easily distinguished from females, even for the neonatal stage (J. L. Brooks, *The Systematics of N. A. Daphnia, Memoirs of the Conn. Academy of Arts and Sciences,* Vol. 23 (1957). The most obvious difference is that males have a rounded without the pointed rostrum of the female, and males have elongated first antennae relative to females.

Toxicity data has been compared for 27 substances (pesticides, metals, PCB's) of fathead minnows and Daphnia (Maki, A. W., *J. Fish Res. Board Canada,* 36:411–421 (1979)). It was concluded that Daphnia were a short-term attractive alternative to the longer-term fish (vertebrate) testing. Daphnia have a very flexible sex ratio, varying from zero (asexual reproduction) to at least 50% (Dodson et al., *Envir. Health Perspectives,* 103 (Special Suppl. No. 4): 7–11 (1996)). Male production is induced by various environmental signals such as short day length, and crowding which produces a chemical signal. Because the ratio is not determined genetically as in most animals where the ratio is close to 50%, it is possible to use small changes in the sex ratio as a bioassay endpoint, in addition to the more standard endpoints of fecundity, survival, and morphology. Because sex ratio is not fixed it is possible to influence the developmental mechanism with test chemicals.

Although not intended to limit the invention to a particular theory, Daphnia sex ratio is likely the result of an endocrine system that transfers environmental signals such as day length or chemical signals, to the developing egg or embryo, just as it occurs in vertebrates. Although little is known about the Daphnia endocrine system, it is in many ways similar to that of vertebrates, even humans. For example, retinoids are growth factors during vertebrate embryogenesis and signals used for maintenance in adult vertebrates. Retinoids are somewhat structurally similar to the juvenile hormones of arthropods, and retinoids have displayed effects similar to those of juvenile hormones on insect metamorphosis, embryogenesis and reproduction. Conversely, methoprene, an artificial juvenile hormone controlling development in arthropods, can stimulate gene transcription in mammals by activating retinoid X receptors (Harmon, et al., *Proc. Natl. Acad. Sciences USA* 92(13) :6157–6160 (1995)). Thus, a specific class of chemical signals may have similar effects in arthropods and vertebrates.

Vertebrates and arthropods use similar steroid chemicals as endocrine signals. For example, vertebrates use estrogen and testosterone, while arthropods use the steroid ecdysone. The vertebrate hormone estradiol-17β also occurs in copepods. Vertebrate steroids can be metabolized by Daphnia, which are especially sensitive to vertebrate androgens. The similarities between vertebrate and arthropod endocrine processes are such that a chemical that disrupts one hormonal system could likely disrupt the other (Zou, E. M. and M. Fingerman, *Ecotoxicology and Envir. Safety* 38:281–285 (1998); Barry, M. J., *J. Plankton Research* in press, (1998).

Dieldrin, one of two known endocrine disrupters tested, reduced male production. This dieldrin finding is contrary to results of an earlier study that found no effect of dieldrin on sex ratio (Zou et al., *Bull. Environ. Contamin. Toxicol.*58:596–602 (1998). The present assay differed from Zou's study by the use of much larger sample sizes which provided greater resolving power (statistical power) allowing the determination that dieldrin reduces sex ratio above about 30 ppb, a value lower than previously suspected of being biologically significant to Daphnia.

A decrease in sex ratio can occur via several basic mechanisms during early development, including:

1) Higher male mortality, with female production remaining the same. However, it was observed that the total number of offspring was not affected by dieldrin exposure.

2) Increase in female production, with an increase in total fecundity. However, there was no evidence that exposure to dieldrin increased fecundity.

3) A change in embryonic developmental rate, e.g., faster female maturation or slower male maturation induced by dieldrin exposure. However, male and female neonates are released at the same time from the adult's brood chamber.

4) Suppression of feeding rate or food quality which would also reduce total fecundity.

5) Seasonality which would not affect sex ratio in a 6-day bioassay.

6) A shift in the developmental process that results in fewer males and more females, with no change in fecundity.

The results of the bioassay supports the interpretation that dieldrin is an exogenous agent that interferes with the action of natural hormones in the Daphnia embryo that are responsible for reproduction development, i.e., dieldrin shows endocrine disruption activity in Daphnia. This endocrine disruption activity has two implications, one for aquatic ecology and one for human health.

Aquatic Ecology. Chemicals that change Daphnia development or reproduction are clearly of ecological concern. Daphnia is an ecologically important algae-consumer and fish-food in lakes all over the world. In particular, a decrease in the number of males has the potential of reducing Daphnia's ecological success over many generations, because sexual production is thought essential for preparing a population for changes in the environment. Any chemical that interferes with normal Daphnia ecology will also have indirect effects on water quality and fish production.

Evidence indicates that Daphnia reproduction has changed during the last century (Dodson et al., *Envir. Health Perspectives* 103 (Special Suppl. No. 4) 7–11 (1996). In Lake Mendota, Wisconsin, Daphnia, which produces up to 50% males in the late 1800s, currently produces less than 5% males. One possibility for this change is the introduction of endocrine disrupters in to the environment beginning in the 1940s.

There is interest in synergistic effects of chemical mixtures and environmental factors because mixtures of chemicals are the norm in aquatic habitats. In the case of dieldrin and endosulfan, there was no evidence for greater-than-additive (synergistic) or enhanced effect of the mixture of these two pesticides. The lack of synergism in Daphnia is consistent with results of other studies of these two chemicals at the molecular level (Ramamoorthy et al., *Endocrinology* 138:1520–1527 (1997).

Human Health. Dieldrin, a chemical known to be an endocrine disrupter in vertebrates, also affects development and reproduction in Daphnia. The result shows that the present Daphnia bioassay can be used as a rapid screen to detect chemicals of potential concern for human health. Daphnia can be useful as a whole-animal invertebrate "canary down the mine shaft" that can provide a useful screen for endocrine disruption for both environmental and human health.

What is claimed is:

1. A bioassay for testing a sample for the presence of a chemical substance that interferes with endocrine function in an animal, comprising:

maintaining a test sample and a control medium under conditions to induce sexual reproduction in Daphnia, the test sample and control each containing an effective number of adult, oviparous Daphnia of a single clone for crowding; and comparing endpoints that indicate a deviation from normal Daphnia sexual reproduction in the test sample and control to determine the presence or absence of the chemical substance;

whereby the presence of an endocrine disrupter substance is indicated by a variance between the test sample and the control of the sex ratio, the ratio of males:total offspring the number of resting eggs, the number of neonates with a morphological abnormality the number of neonates with a behavioral abnormality the nutritional status of the offspring, or a combination thereof.

2. The bioassay according to claim 1, wherein the endpoints include survivorship of adults and neonates, fecundity, and at least one of the following endpoints: number of male offspring, sex ratio of males:total offspring (neonates), number of resting eggs, number of offspring having a morphological abnormality, number of offspring having a behavioral abnormality, and nutritional status of offspring.

3. The bioassay according to claim 1, wherein the sample and the control are maintained at a temperature of about 17–25° C., and a light:dark photoperiod of about 6–9 hours light to about 18-15 hours dark.

4. The bioassay according to claim 1, further comprising changing the sample and the control on about day 3–4 of the assay period, and discarding the neonate Daphnia from the sample and the control.

5. The bioassay according to claim 2, wherein the endpoints are measured in multigenerations of the Daphnia clone.

6. The bioassay according to claim 1, further comprising: an initial step of determining the sublethal concentration of the test sample.

7. The bioassay according to claim 6, wherein the sublethal concentration of the test sample is determined by maintaining a control medium and a series of aqueous dilutions of the test sample under growth conditions to induce sexual reproduction in Daphnia, each of the dilutions and the control containing an effective number of adult, oviparous Daphnia of a single clone for crowding;

comparing fecundity and survivorship in the dilutions and the control to determine the dilution having the highest concentration of the test sample at which survivorship and fecundity are maintained at about the same level as the control; and using said dilution of the test sample in the assay.

8. The bioassay according to claim 1, wherein the Daphnia clone produces about 5–70% males of the total offspring under the control conditions.

9. The bioassay according to claim 2, wherein the morphological abnormality is identified by reduced or absent terminal setae on the second antennae, a forward curved tail spine, reduced swimming ability, or a combination thereof.

10. The bioassay according to claim 2, wherein the behavioral abnormality is identified by abnormal swimming or abnormal motility.

11. The bioassay according to claim 1, further comprising: conducting an assay to identify the chemical substance in the test sample.

12. The bioassay according to claim 1, wherein the chemical substance is an herbicide, insecticide, fungicide, xenobiotic, plasticizer, phytohormone, phytoestrogen, organic solvent, or a combination thereof.

13. The bioassay according to claim 12, wherein the chemical substance is selected from the group consisting of estradiol, diethylstilbestrol, kepone, dichlorodiphenyltrichloroethane, dichlorodiphenyldichloroethane, 1-hydroxychlordene, chlordane, zearalenone, coumestrol, nonylphenol, butylphenol, pentylphenol, isopentylphenol, polychlorinated biphenyl, chlorpyrifols, pentachlorophenol, atrazine, carbaryl, endosulfan, ethanol, and derivatives thereof.

14. The bioassay according to claim 1, wherein the substance is atrazine.

15. A bioassay for determining the sublethal level of toxicity of a substance, comprising:
   maintaining a control medium and a series of dilutions of the substance in an aqueous medium under growth conditions to induce sexual reproduction in Daphnia, each of the dilutions and the control containing an effective number of adult, oviparous Daphnia of a single clone for crowding;
   determining the sublethal level of toxicity of the substance by comparing fecundity and survivorship of Daphnia in the dilutions and the control to identify the dilution having the highest concentration of the substance at which survivorship and fecundity are at about the same level as the control.

16. The bioassay according to claim 15, further comprising:
   comparing one or more endpoints that indicate a deviation from normal Daphnia sexual reproduction in the test sample dilution having the highest sublethal concentration of the substance.

17. The bioassay according to claim 15, wherein the endpoints include the number of male offspring, number of female offspring, sex ratio of males: total offspring, number of resting eggs, and number of offspring displaying a morphological abnormality, number of offspring displaying a behavioral abnormality, and nutritional status of offspring.

18. A bioassay for determining the presence of a toxic chemical substance in a sample, comprising:
   maintaining a control medium and the sample in an aqueous medium under growth conditions to induce sexual reproduction in Daphnia, each of the control and the sample containing an effective number of adult, oviparous Daphnia of a single clone for crowding; and
   comparing fecundity and survivorship of the Daphnia in the sample and the control;
   wherein the presence of a toxic substance in the sample is determined by a lower level of fecundity, and survivorship of the Daphnia in the sample compared to the control.

19. A kit for use in conducting a Daphnia reproductive bioassay on an aqueous sample to detect a substance that interferes with endocrine function in an animal, comprising, in association and separately packaged:
   a culture of a clone of Daphnia capable of producing at least about 5–70% males of the total offspring under control conditions; instructions for conducting the Daphnia bioassay according to claim 1; a data scoring sheet; and an algal food source for the Daphnia.

20. The kit according to claim 19, further comprising:
   a container for the sample; a container for the control; a container for observing the Daphnia; a device for manipulating the Daphnia; a growth medium for culturing the Daphnia and the algae; or any combination thereof.

* * * * *